US010946715B2

(12) United States Patent
Yamada et al.

(10) Patent No.: US 10,946,715 B2
(45) Date of Patent: Mar. 16, 2021

(54) AIR-BLOWING SYSTEM HAVING DISCHARGE DEVICE

(71) Applicant: Panasonic Intellectual Property Management Co., Ltd., Osaka (JP)

(72) Inventors: Yusuke Yamada, Shiga (JP); Akihide Sugawa, Shiga (JP); Takeshi Yano, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 51 days.

(21) Appl. No.: 16/327,540

(22) PCT Filed: Aug. 28, 2017

(86) PCT No.: PCT/JP2017/030648
§ 371 (c)(1),
(2) Date: Feb. 22, 2019

(87) PCT Pub. No.: WO2018/043365
PCT Pub. Date: Mar. 8, 2018

(65) Prior Publication Data

US 2019/0193513 A1 Jun. 27, 2019

(30) Foreign Application Priority Data

Aug. 30, 2016 (JP) ............................. JP2016-168035

(51) Int. Cl.
*B60H 1/00* (2006.01)
*B05B 5/057* (2006.01)
(Continued)

(52) U.S. Cl.
CPC ............ *B60H 1/00564* (2013.01); *A61L 9/14* (2013.01); *B05B 5/057* (2013.01); *B60H 1/00* (2013.01);
(Continued)

(58) Field of Classification Search
CPC .. B60H 1/00564; B60H 1/0055; B60H 1/242; B60H 1/004; B60H 1/246; B60H 1/243;
(Continued)

(56) References Cited

U.S. PATENT DOCUMENTS 6,705,672 B2 * 3/2004 Shikata .............. B60H 1/00528
296/208
9,187,052 B2 * 11/2015 Kimura ..................... B60L 1/02
(Continued)

FOREIGN PATENT DOCUMENTS

EP 1980433 A1 10/2008
EP 1995527 A1 11/2008
(Continued)

OTHER PUBLICATIONS

International Search Report issued in Application No. PCT/JP2017/030648 dated Nov. 28, 2017, with English translation.
(Continued)

*Primary Examiner* — D Glenn Dayoan
*Assistant Examiner* — Sunsurraye Westbrook
(74) *Attorney, Agent, or Firm* — McDermott Will & Emery LLP

(57) ABSTRACT

An air-blowing system having discharge device includes an air supply passage, and a discharge device provided for generating active ingredients and is disposed outside the air supply passage. Further, the air-blowing system having discharge device includes an introducing pipe having an one end connected to a discharge device and an other end disposed in the air supply passage, and provided for introducing the active ingredients into the air supply passage. The introducing pipe has an opening face on the other end. In the introducing pipe, the opening face and a main stream direction of an air flow, which flows through the air supply passage at a predetermined point of the opening face, are
(Continued)

disposed substantially parallel to each other. Thus, an air-blowing system having discharge device with a simplified configuration is provided.

12 Claims, 7 Drawing Sheets

(51) Int. Cl.
*A61L 9/14* (2006.01)
*B60H 3/00* (2006.01)
*B60H 1/34* (2006.01)

(52) U.S. Cl.
CPC ................. *B60H 1/34* (2013.01); *B60H 3/00* (2013.01); *B60H 1/00871* (2013.01)

(58) Field of Classification Search
CPC .............. B60H 1/245; B60H 2001/003; B60H 1/00295
USPC ... 296/208, 70, 192, 214, 108, 97.23, 96.21, 296/93; 180/65.1, 402, 165, 291, 65.25, 180/90
See application file for complete search history.

(56) References Cited

U.S. PATENT DOCUMENTS 9,751,385 B2* 9/2017 Yano .................... B60H 3/0071
9,890,966 B2* 2/2018 Mueller ................. B62D 25/16
2008/0032618 A1* 2/2008 Katoh ................ B60H 1/00564 454/143
2008/0217963 A1* 9/2008 Brunard ................. B60H 1/242 296/208
2009/0321544 A1 12/2009 Akisada et al.
2010/0237660 A1* 9/2010 Grammer ............... B62D 25/16 296/208
2011/0259980 A1 10/2011 Akisada et al.

FOREIGN PATENT DOCUMENTS

JP 62-131913 U 8/1987
JP 2005-289177 A 10/2005
JP 2008-094181 A 4/2008
JP 4396672 B2 1/2010
JP 2011-007443 A 1/2011
JP 2011-087273 A 4/2011
JP 5276307 B2 8/2013
JP 2013-221631 A 10/2013
WO 2010/150770 A1 12/2010

OTHER PUBLICATIONS

Extended European Search Report dated Jul. 9, 2019 issued in corresponding European Patent Application No. 17846370.9.

* cited by examiner

AIR-BLOWING SYSTEM HAVING DISCHARGE DEVICE

RELATED APPLICATIONS

This application is the U.S. National Phase under 35 U.S.C. § 371 of International Application No. PCT/JP2017/030648, filed on Aug. 28, 2017, which in turn claims the benefit of Japanese Application No. 2016-168035, filed Aug. 30, 2016, the disclosures of which are incorporated by reference herein.

TECHNICAL FIELD

The present invention relates to an air-blowing system having discharge device.

BACKGROUND ART

Conventionally, there has been known an air-blowing system having discharge device which blows off air containing active ingredients to the outside of the air-blowing system (for example, see PTL 1).

The air-blowing system having discharge device described in PTL 1 includes a discharge device mounted on the air-blowing system. The air-blowing system has an air supply passage having an air outlet from which air is blown off. In the air-blowing system, active ingredients generated by the discharge device are introduced into the air supply passage. Accordingly, air containing active ingredients is blown off to the outside of the air-blowing system.

The discharge device is disposed outside the air supply passage. The discharge device includes a fan which functions as an air blower for introducing active ingredients generated by the discharge device into the air supply passage.

Active ingredients generated by the discharge device are pressurized to an air internal pressure or more of air which flows through the air supply passage by the fan. At this time, one end of an introducing pipe is connected to the discharge device, and the other end of the introducing pipe is disposed in the air supply passage. Then, the active ingredients generated by the discharge device are introduced into the air supply passage through the introducing pipe. Accordingly, it is possible to suppress the exposure of the discharge device to high temperature air or low humidity air which flows through the air supply passage. As a result, active ingredients can be generated by the discharge device without being affected by air which flows through the air supply passage.

Further, in the above-mentioned air-blowing system having discharge device, the other end side of the introducing pipe is disposed along an air flow passage in the air supply passage. A distal end opening of the introducing pipe on the other end side is arranged to be directed toward an air outlet side. With such a configuration, active ingredients are effectively carried on air which flows through the air supply passage and is blown off to the outside of the air-blowing system from the air outlet, and are blown off to the outside of the air-blowing system.

Further, there has been proposed an air-blowing system having discharge device where one end of an introducing pipe is connected to a discharge device and the other end of the introducing pipe is connected to an inner peripheral side of a bent portion formed in an air supply passage (for example, see PTL 2).

The air-blowing system having discharge device described in PTL 2 is configured to induce active ingredients generated by a discharge device disposed outside the air supply passage into the air supply passage by making use of a negative pressure generated on the inner peripheral side of the bent portion in the air supply passage.

However, in the air-blowing system having discharge device described in the above-mentioned PTL 1, the discharge device per se includes a fan. Accordingly, the size and cost of the discharge device are increased. Further, there is also a concern that vibrations and uncomfortable noises occur due to an operation of the fan.

On the other hand, the air-blowing system having discharge device described in PTL 2 is configured to discharge active ingredients into the air supply passage by making use of a locally negative pressure generating portion. Accordingly, a connection position of the introducing pipe is restricted and hence, a trouble easily occurs in designing the air-blowing system. Further, in the case where deflectors or the like are disposed at an air outlet of the air supply passage, the negative pressure generating portion changes or disappears depending on an interval or an angle of the deflectors. Accordingly, there is a concern that a generated negative pressure cannot be effectively utilized.

CITATION LIST

Patent Literature

PTL 1: JP 4396672 B2
PTL 2: JP 5276307 B2

SUMMARY OF THE INVENTION

It is an object of the present invention to provide an air-blowing system having discharge device which can introduce active ingredients to the inside of an air supply passage in a state where a connection position of an introducing pipe to the air supply passage is not restricted without using a pressurizing fan in the discharge device.

The air-blowing system having discharge device according to the present invention includes: an air supply passage having an air outlet from which air is blown off; and a discharge device provided for generating active ingredients and disposed outside the air supply passage. The air-blowing system having discharge device also includes an introducing pipe having one end connected to the discharge device and the other end disposed in the air supply passage, the introducing pipe being provided for introducing active ingredients into the air supply passage. The other end of the introducing pipe introduces an opening face. The introducing pipe is arranged such that, in a state where the other end side of the introducing pipe is disposed in the air supply passage, the opening face and a main stream direction of an air flow which flows through the air supply passage at a predetermined point of the opening face are substantially parallel to each other.

With such a configuration, a fan in the discharge device can be omitted. Further, the degree of freedom in connecting the introducing pipe is enhanced.

DESCRIPTION OF EMBODIMENTS

Hereinafter, exemplary embodiments of the present invention will be described with reference to the drawings. The exemplary embodiments should not be construed to limit the scope of the present invention. Substantially identical constitutional elements are included in the plurality of exemplary embodiments described hereinafter respectively. Accordingly, in the following description, common symbols are given to the substantially identical constitutional elements, and the repeated explanation of these constitutional elements is omitted.

First Exemplary Embodiment

Hereinafter, the schematic configuration of an air-blowing system having discharge device according to a first exemplary embodiment of the present invention is described with reference to FIG. 1 to FIG. 3.

Hereinafter, the description is made by taking a device where an electrostatic atomization device is mounted on a vehicle-use air conditioner, which is mounted on vehicle 1, as the air-blowing system having discharge device as an example. The vehicle-use air conditioner is an example of an air-blowing system. The electrostatic atomization device is formed of a discharge portion, a liquid supply portion and the like, and is an example of the discharge device. The electrostatic atomization device generates charged fine water particles of a nanometer size which contain radicals as active ingredients.

Figure 1:
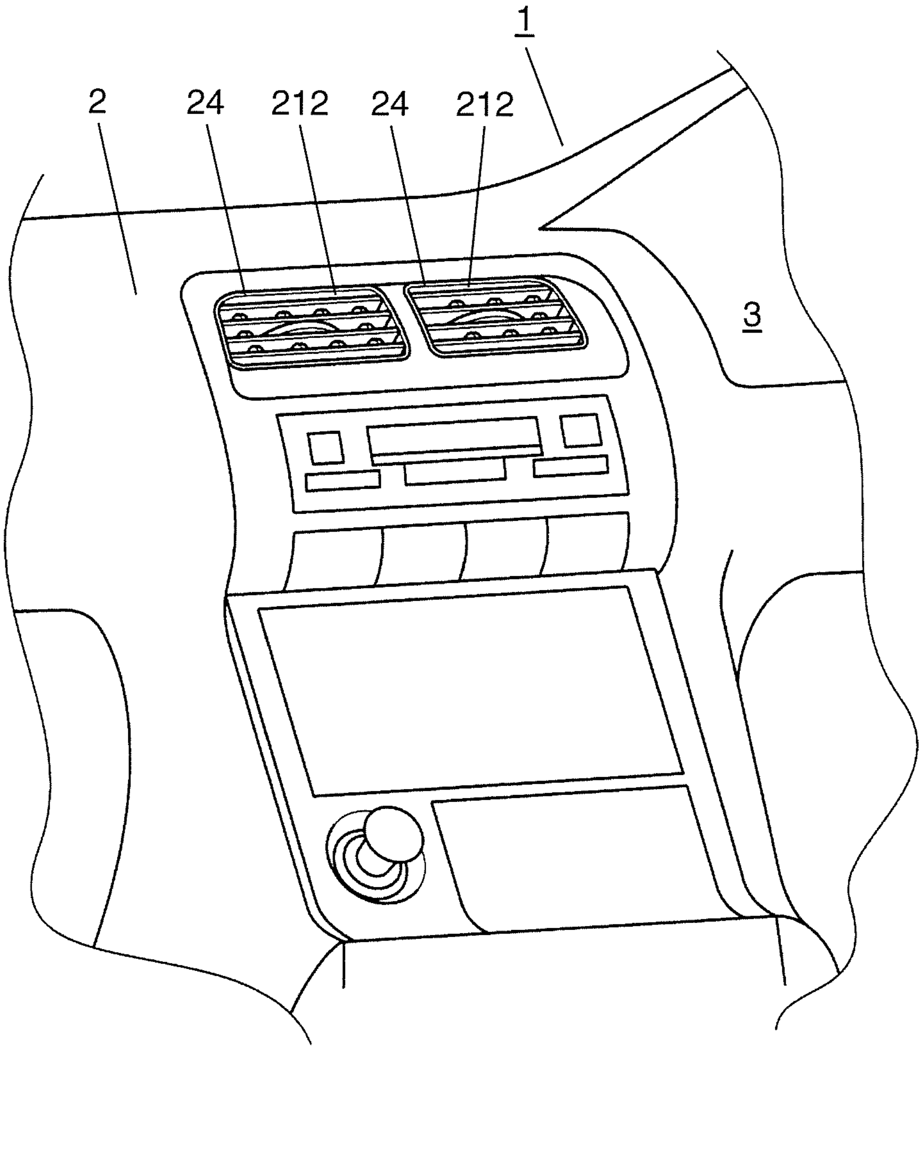
FIG. 1 is a view schematically showing one example of an air-blowing system having discharge device according to a first exemplary embodiment of the present invention in a state where the air-blowing system having discharge device is disposed on a vehicle.
Figure 2:
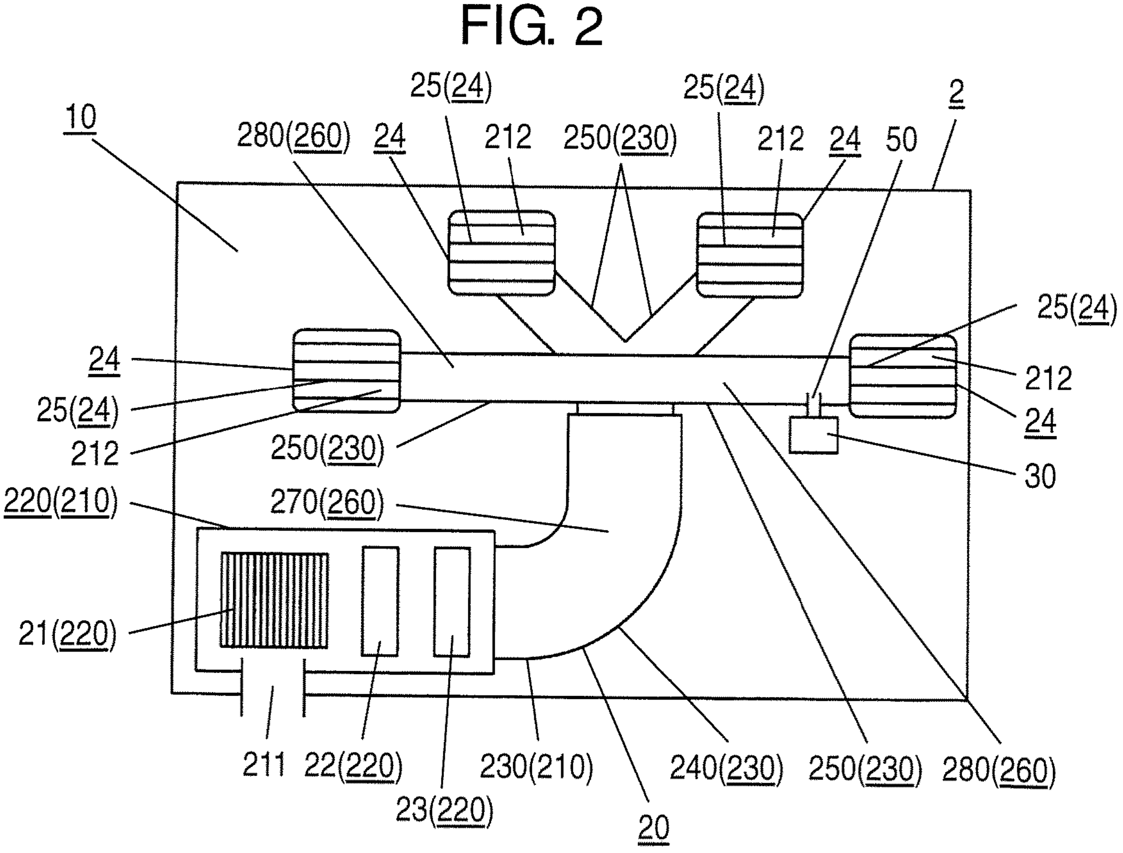
FIG. 2 is a view schematically showing the air-blowing system having discharge device according to the exemplary embodiment.

As shown in FIG. 1 and FIG. 2, air conditioner having discharge device 10 according to the present exemplary embodiment includes vehicle-use air conditioner 20 which forms the air-blowing system, electrostatic atomization device 30 which forms the discharge device and the like, and is mounted on vehicle 1.

To be more specific, discharge device equipped air conditioner 10 is disposed in instrument panel 2 which defines cabin 3 (disposed outside cabin 3).

Vehicle-use air conditioner 20 includes housing 210 having suction port 211 and one or more air outlets 212. Air outside vehicle-use air conditioner 20 is taken into cabin 3 through suction port 211. In air outlets 212, active ingredients described later are contained in air taken into cabin 3, and the air is blown off to the outside of vehicle-use air conditioner 20. Housing 210 is formed using a resin such as polypropylene (PP) and polybutylene terephthalate (PBT), for example.

In the inside of housing 210, air conditioning portion 220, pipe portion 230 and the like are further disposed. Air conditioning portion 220 is continuously formed with suction port 211, and adjusts, for example, a temperature and humidity of air taken into cabin 3 through suction port 211. Pipe portion 230 is continuously formed with air conditioning portion 220, and air supply passage 260 through which air adjusted by air conditioning portion 220 flows is formed in pipe portion 230.

In air conditioning portion 220, blower 21, filter 22, evaporator 23 and the like are disposed. Blower 21 generates the flow of air which becomes an object to be blown. Filter 22 removes foreign substances in sucked air. Evaporator 23 adjusts a temperature or the like of sucked air. Suction port 211 of housing 210 is configured in a switchable manner such that suction port 211 selectively communicates with either the outside of cabin 3 or inside of cabin 3 by a switching portion (not shown in the drawing).

Pipe portion 230 further includes pipe body 240 continuously formed with air conditioning portion 220, one or more branch pipes 250 continuously formed with a downstream side of pipe body 240, and the like. That is, air supply passage 260 is formed of air supply passage body 270 formed in pipe body 240, and branch passages 280 formed in respective branch pipes 250. Air outlets 212 of housing 210 are disposed on a downstream side of branch passages 280 formed in respective branch pipes 250.

That is, vehicle-use air conditioner 20 is disposed in instrument panel 2 (disposed outside cabin 3) in a state where respective air outlets 212 communicate with cabin 3.

In vehicle-use air conditioner 20 having the above-mentioned configuration, firstly, the flow of air is generated by supplying electricity to blower 21. Accordingly, air outside cabin 3 or air inside cabin 3 is taken into air conditioning portion 220 through suction port 211 of housing 210.

Air taken into air conditioning portion 220 passes through filter 22, so that foreign substances in air are removed. Then, air from which the foreign substances are removed is introduced into evaporator 23 where a temperature or the like of air is adjusted.

Air whose temperature is adjusted by evaporator 23 (hereinafter also referred to as "adjusted air") is introduced in air supply passage 260, and is blown off into cabin 3 through air outlets 212 of housing 210. In the present exemplary embodiment, adjusted air is firstly introduced into air supply passage body 270 from air conditioning portion 220. The introduced adjusted air passes through air supply passage body 270, and is introduced into one or more branched branch passages 280. Then, the adjusted air introduced in branch passages 280 passes through branch passages 280, and is blown off into cabin 3 from air outlets 212 of housing 210 formed on a downstream side of branch passages 280.

Finisher 24 is mounted on respective air outlets 212 of housing 210. Finisher 24 is formed in a frame shape using a synthetic resin such as polypropylene, for example, and is mounted on a downstream end (air outlet 212) of branch pipe 250.

Finisher 24 has a plurality of partition walls 25, for example.

Accordingly, in a front view of air outlet 212 of housing 210, one or more opening portions 212*a* are defined by finisher 24 and partition walls 25. That is, in a front view of air outlet 212 of the present exemplary embodiment, at least a portion of air outlet 212 has one or more opening portions 212*a* defined by partition wall 25.

Further, partition wall 25 includes air direction adjusting plate 25*a* which adjusts the direction of air blown off from air outlet 212.

That is, for example, a plurality of (four in FIG. 3) horizontal partition walls 25*b*, and, for example, a plurality of (five in FIG. 3) air direction adjusting plates 25*a* are mounted on finisher 24. To be more specific, horizontal partition walls 25*b* are disposed so as to extend approximately horizontally (including horizontally) in finisher 24. Air direction adjusting plates 25*a* are mounted on an upstream side of horizontal partition walls 25*b* in branch passages 280 (in air supply passages 260). With this configuration, air direction adjusting plates 25*a* are rotatably mounted about a rotary axis extending approximately vertically (including vertically) in branch passages 280.

That is, opening portions 212*a* are defined by finisher 24, horizontal partition walls 25*b* extending in the horizontal direction, and air direction adjusting plates 25*a* extending in the vertical direction.

The respective air direction adjusting plates 25*a* are connected to each other by link 27. With this configuration, among five air direction adjusting plates 25*a* shown in FIG. 3, tab portion 26 is formed on air direction adjusting plate 25*a* positioned at the center in the longitudinal direction, for example. Tab portion 26 is mounted on air direction adjusting plate 25*a* in a slidable manner in the lateral direction with a predetermined stroke.

Air direction adjusting plate 25*a* on which tab portion 26 is mounted and air direction adjusting plates 25*a* which are connected to air direction adjusting plate 25*a* by means of link 27 are rotated in the lateral direction in an interlocking manner with manipulation of tab portion 26 in the lateral direction. Accordingly, the direction of air blown off into cabin 3 from air outlets 212 of housing 210 (air direction) is adjusted laterally.

Figure 3:
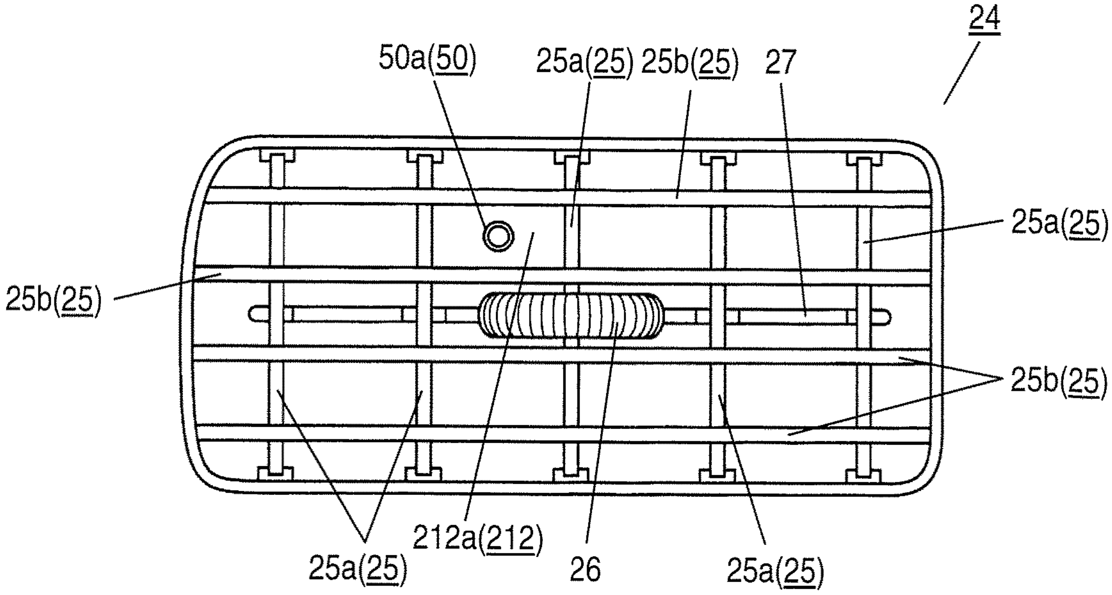
FIG. 3 is a view showing an air outlet of the air-blowing system having discharge device according to the exemplary embodiment as viewed from a front side.

As shown in FIG. 3, the description has been made with respect to the configuration where the direction of air (air direction) is adjustable only in the lateral direction by means of tab portion 26 as an example heretofore. However, the present invention is not limited to such a configuration. For example, horizontal partition wall 25*b* extending in the horizontal direction may be configured to be rotatable about a rotary axis extending in the approximately vertical direction (including the vertical direction). With such a configuration, the direction of air blown off into cabin 3 from air outlets 212 (air direction) is adjustable in the vertical direction as well as in the lateral direction. Further, the direction of air blown off into cabin 3 from air outlets 212 (air direction) may be adjustable only in the vertical direction by tab portion 26.

Air conditioner having discharge device 10 which is an example of the air-blowing system having discharge device according to the present exemplary embodiment is configured as described above.

The configuration of electrostatic atomization device 30 which is an example of the discharge device of air conditioner having discharge device 10 is described hereinafter with reference to FIG. 4. Electrostatic atomization device 30 generates charged fine water particles 40 which are active ingredients.

Figure 4:
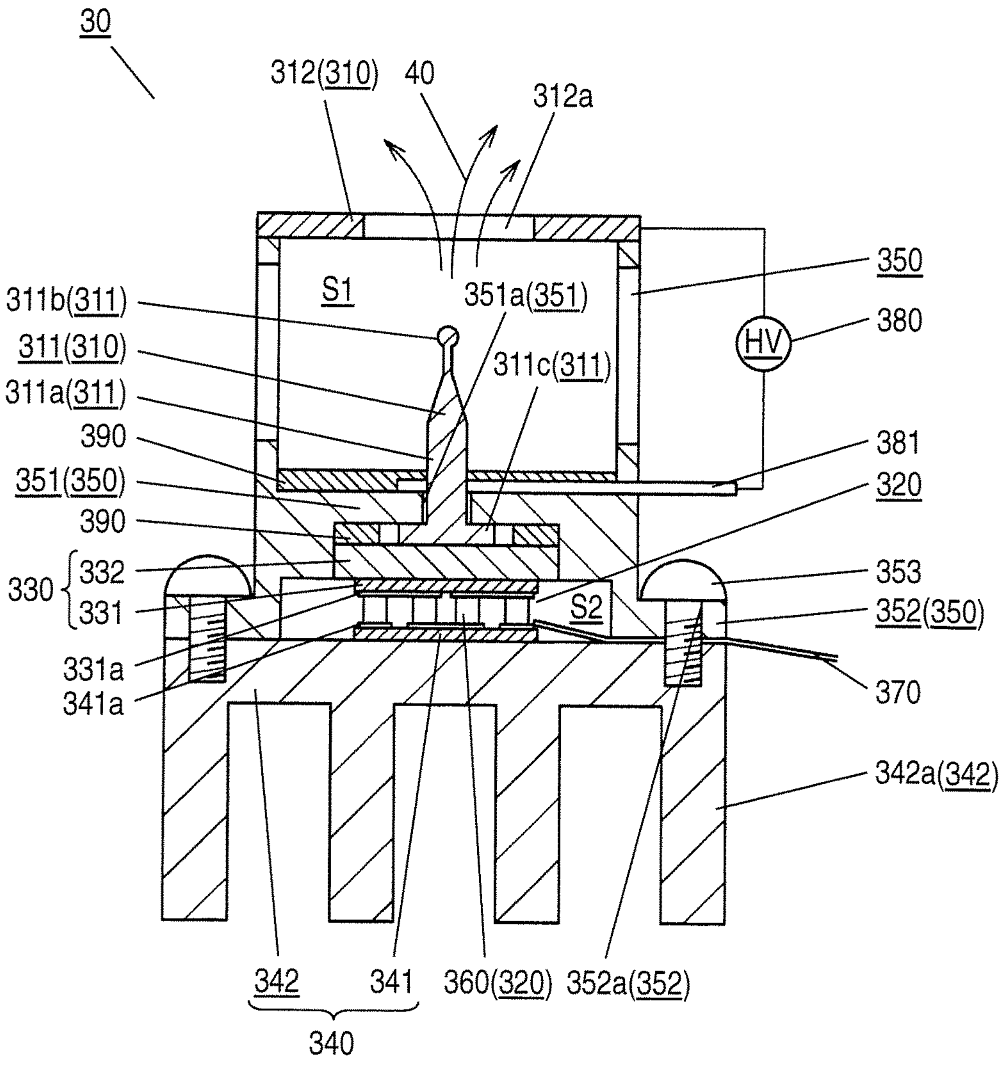
FIG. 4 is a view schematically showing a discharge device of the air-blowing system having discharge device according to the exemplary embodiment.

As shown in FIG. 4, electrostatic atomization device 30 according to the present exemplary embodiment is formed of at least discharge portion 310, Peltier unit 320, and the like. Discharge portion 310 includes discharge electrode 311 which forms a first electrode, and counter electrode 312 which forms a second electrode, and the like. Peltier unit 320 has cooling portion 330 and heat radiation portion 340, and forms a liquid supply portion.

Discharge electrode 311 of discharge portion 310 is connected to a cooling portion 330 side of Peltier unit 320, and cools cooling portion 330 by discharge electrode 311 of discharge portion 310 as desired.

On the other hand, counter electrode 312 of discharge portion 310 is provided on a distal end of support frame 350 connected to Peltier unit 320, and is held by support frame 350. With such a configuration, discharge electrode 311 and counter electrode 312 of discharge portion 310 are fixed at positions where discharge electrode 311 and counter electrode 312 opposedly face each other with a predetermined distance formed therebetween. Counter electrode 312 is not indispensable, and counter electrode 312 can be omitted provided that a high voltage which can generate discharge is applied to discharge electrode 311. Besides a housing in which electrostatic atomization device 30 is stored, charge removing plate may be disposed in an opposedly facing manner with electrostatic atomization device 30.

Cooling portion 330 of Peltier unit 320 includes insulating plate 331, cooling insulating plate 332, and the like. Insulating plate 331 is formed using, for example, alumina, aluminum nitride or the like having high heat conductivity. Cooling insulating plate 332 is formed using, for example, alumina, aluminum nitride or the like having high heat conductivity and high withstand voltage. Circuit 331*a* is formed on one surface side (a lower side in FIG. 4) of insulating plate 331.

On the other hand, heat radiation portion 340 of the Peltier unit 320 includes insulating plate 341, heat radiation plate 342, and the like. Insulating plate 341 is formed using, for example, alumina, aluminum nitride or the like having high heat conductivity. Heat radiation plate 342 is formed using metal such as aluminum or the like, for example, having high heat conductivity. Circuit 341*a* is formed on one surface side (an upper side in FIG. 4) of insulating plate 341. On the other hand, one or more heat radiation fins 342*a* are mounted on one surface side (a lower side in FIG. 4) of heat radiation plate 342.

Circuit 331*a* of cooling portion 330 and circuit 341*a* of heat radiation portion 340 are disposed so as to opposedly face each other. A large number of thermoelectric elements 360 of a BiTe group, for example, are sandwiched in a row between circuit 331*a* and circuit 341*a* which opposedly face each other. In such a configuration, thermoelectric elements 360 disposed adjacently to each other are electrically connected with circuit 331*a*, circuit 341*a* on both sides. Accordingly, electricity is supplied to thermoelectric elements 360 disposed adjacently to each other via a Peltier input lead line 370, and heat is moved from one side to the other side with respect to cooling portion 330 and heat radiation portion 340. As a result, discharge electrode 311 of discharge portion 310 is cooled, so that vapor or the like in air is condensed on discharge electrode 311.

That is, as described above, in discharge device 30 according to the present exemplary embodiment, cooling portion 330 is formed of insulating plate 331 and cooling insulating plate 332 on a cooling side, and heat radiation portion 340 is formed of insulating plate 341 and heat radiation plate 342 on a heat radiation side. Further, discharge device 30 is configured such that heat is transferred from a cooling portion 330 side to a heat radiation portion 340 side through thermoelectric elements 360. With such a configuration, discharge portion 310 can be cooled.

Support frame 350 of discharge device 30 is formed using an insulation material such as a PBT resin, polycarbonate, a PPS resin or the like, for example, and is formed of a sleeve having opening portions on both ends. The opening portions communicate with each other in a penetrating manner.

On an outer periphery of the opening portion on one end side (Peltier unit 320 side) of support frame 350, flange portion 352 for connection to which heat radiation plate 342 is connected is mounted in a protruding manner over the entire circumference. On the opening portion on the other end side of support frame 350 (hereinafter referred to as "mist ejecting port 312*a*"), for example, ring-shaped counter electrode 312 is integrally formed with the opening portion by insert molding, for example.

Flange portion 352 has one or more screw holes 352*a* which penetrate flange portion 352 at equal intervals in the circumferential direction. Flange portion 352 and a peripheral portion of heat radiation plate 342 are threadedly engaged with each other by screws 353 by way of screw holes 352*a*. Accordingly, support frame 350 is connected to Peltier unit 320. The connecting method is not limited to thread engagement. For example, support frame 350 and Peltier unit 320 may be connected to each other by making support frame 350 and Peltier unit 320 adhere to each other using a thermosetting adhesive, for example, while pressing support frame 350 to Peltier unit 320.

Support frame 350 has partition wall 351 extending toward the center from an inner peripheral surface of support frame 350. Partition wall 351 divides an inner space of support frame 350 into two spaces, that is, discharge space S1 and sealing space S2. Communication hole 351*a* is formed at the center of partition wall 351 so as to make discharge space S1 and sealing space S2 communicate with each other. Discharge electrode 311 passes through communication hole 351*a*.

Discharge electrode 311 of discharge portion 310 is formed using a material having high heat conductivity and high electric conductivity such as, for example, aluminum, copper, tungsten, titanium, stainless steel or the like.

Discharge electrode 311 is formed of main body portion 311*a* and a sandwiched portion 311*c* having a diameter larger than main body portion 311*a*, formed in a circular columnar shape. Main body portion 311*a* is formed with a diameter smaller than a diameter of communication hole 351*a* formed in partition wall 351 (including a diameter equal to the diameter of communication hole 351*a*), and has, for example, sharpened discharge electrode end portion 311*b* on a distal end (counter electrode 312 side) of main body portion 311*a*. Sandwiched portion 311*c* is formed on a proximal end side (Peltier unit 320 side) of main body portion 311*a*, and is formed with a diameter larger than the diameter of communication hole 351*a* formed in partition wall 351.

Main body portion 311*a* of discharge electrode 311 is fitted in communication hole 351*a* formed in partition wall 351. With such a configuration, Peltier unit 320 is connected to support frame 350. At this time, with respect to main body portion 311*a* of discharge electrode 311, a discharge electrode end portion 311*b* side is disposed in discharge space S1, and sandwiched portion 311*c* of discharge electrode 311 is disposed in sealing space S2. With such a configuration, sandwiched portion 311*c* of discharge electrode 311 is sandwiched between partition wall 351 of support frame 350 and cooling insulating plate 332 of Peltier unit 320. As a result, sandwiched portion 311*c* of discharge electrode 311 is pressed to a cooling portion 330 side of Peltier unit 320, and sandwiched portion 311*c* and cooling portion 330 are connected to each other.

That is, support frame 350 functions as a sandwiching member for fixing cooling portion 330 of Peltier unit 320 and discharge electrode 311 in a connection state. Simultaneously, support frame 350 also functions as a sealing member which holds the inside of Peltier unit 320 in a sealing state such that moisture does not intrude into circuit 331*a*, circuit 341*a*, and thermoelectric elements 360 disposed in the inside of Peltier unit 320.

In this case, a space between cooling insulating plate 332 of Peltier unit 320 and partition wall 351 and an upper surface of partition wall 351 are sealed by sealing resin 390 made of an epoxy resin, for example. Accordingly, the inside of Peltier unit 320 is sealed with more certainty. As shown in FIG. 4, sealing by sealing resin 390 is not limited to the space between support frame 350 and cooling insulating plate 332 and the space between support frame 350 and discharge electrode 311. For example, sealing resin 390 may be provided for performing sealing by filling sealing resin 390 into the inside of Peltier unit 320, for example.

Further, main body portion 311*a* of discharge electrode 311 is connected to one end side of high voltage lead line 381 in discharge space S1 of support frame 350. On the other hand, the other end side of high voltage lead line 381 is pulled out to the outside of support frame 350 and is connected to high voltage applying portion 380. High voltage lead line 381 is formed using metal such as stainless steel or copper, electric conductive plastic or the like, for example. Further, high voltage applying portion 380 which is electrically connected to discharge electrode 311 through high voltage lead line 381 is electrically connected with counter electrode 312 disposed above support frame 350. With such a configuration, a high voltage generated by high voltage applying portion 380 is applied between discharge electrode 311 and counter electrode 312. As a result, it is possible to produce an electric discharge which generates active ingredients between discharge electrode 311 and counter electrode 312.

Electrostatic atomization device 30 which is an example of the discharge device of air conditioner having discharge device 10 is configured as described above.

Hereinafter, the manner of operation and advantageous effects of electrostatic atomization device 30 having the above-mentioned configuration is described.

Firstly, in electrostatic atomization device 30 having the above-mentioned configuration, electricity is supplied to thermoelectric elements 360 in a sealed state due to connection between support frame 350 and heat radiation plate 342 through Peltier input lead line 370. When electricity is supplied to the respective thermoelectric elements 360, the transfer of heat in the same direction is generated in the respective thermoelectric elements 360. Then, due to such heat transfer, discharge electrode 311 is cooled through cooling portion 330 connected to a cooling side of thermoelectric elements 360. Accordingly, in discharge space S1 of support frame 350, air around discharge electrode 311 is cooled. As a result, moisture such as vapor in air is formed into a liquid by condensation or the like, so that water is produced on a surface of discharge electrode 311.

Next, water is produced particularly on discharge electrode end portion 311*b* of discharge electrode 311, and in a state where water is held on discharge electrode end portion 311*b*, high voltage is applied between discharge electrode 311 and counter electrode 312 by high voltage applying portion 380. At this time, high voltage applying portion 380 applies a high voltage such that a discharge electrode end portion 311*b* side of discharge electrode 311 becomes a minus electrode and an electric charge is concentrated on the minus electrode. Accordingly, water held on discharge electrode end portion 311*b* receives large energy and repeats a Rayleigh breakup. As a result, a large amount of charged fine water particles 40 of a nanometer size which are the above-mentioned active ingredients are generated. Generated charged fine water particles 40 move toward counter electrode 312 which opposedly faces discharge electrode 311. Then, charged fine water particles 40 pass through mist ejecting port 312*a* and are blown off to the outside of electrostatic atomization device 30 (the inside of cabin 3 in the present exemplary embodiment).

Charged fine water particles 40 produced by electrostatic atomization device 30 contain radicals such as superoxide radicals or hydroxyl radicals, for example. These radicals have effects such as odor removal, suppression of growth of viruses and mold fungus, and deactivation of allergens. Accordingly, for example, by blowing off charged fine water particles 40 containing radicals to the inside of cabin 3, it is possible to remove odor ingredients in air in cabin 3 and to perform odor removal of odor ingredients adhering to wall surfaces and seats in cabin 3. Further, it is also possible to suppress allergen such as pollen brought into cabin 3 in a state pollen adheres to closing of a person.

In the above-mentioned exemplary embodiment, the description is made by taking the electrostatic atomization device as the discharge device as an example. However, the present invention is not limited thereto. For example, the Peltier unit which forms the liquid supply portion may be omitted, and an ion generator which does not generate charged fine water particles but generates air ions such as minus ions or plus ions may be used as the discharge device. In this case, the ion generator generates hydroxyl radicals or the like. With such a configuration, it is possible to acquire substantially the same advantageous effects as the above-mentioned advantageous effects acquired by electrostatic atomization device 30.

Electrostatic atomization device 30 operates as described above thus acquiring the above-mentioned manner of operation and advantageous effects.

The air-blowing system having discharge device of the present exemplary embodiment is configured to blow off air containing charged fine water particles 40 generated by the above-mentioned electrostatic atomization device 30 into the inside of cabin 3 from air outlet 212 of at least one branch passage 280 out of one or more branched branch passages 280.

In this case, a configuration is considered where electrostatic atomization device 30 is disposed in the inside of branch passage 280. That is, charged fine water particles 40 are generated by electrostatic atomization device 30 disposed in the inside of branch passage 280, and charged fine water particles 40 are carried on air flow R1 (see FIG. 5) in the inside of branch passage 280. With such a configuration, a configuration is considered where charged fine water particles 40 are dispersed in the inside of cabin 3.

However, when electrostatic atomization device 30 is disposed in the inside of air supply passage 260 of vehicle-use air conditioner 20 provided with equipment such as evaporator 23 and blower 21, electrostatic atomization device 30 is exposed to air (high temperature air and/or low humidity air) adjusted by air conditioning portion 220. When electrostatic atomization device 30 is exposed to adjusted air, there may be a case where water supplied to discharge electrode 311 for making electrostatic atomization is evaporated by adjusted air. Accordingly, there may be a case where electrostatic atomization due to discharging of water is disturbed.

Electrostatic atomization device 30 makes moisture in air condensed by cooling discharge electrode 311 thus generating water for performing electrostatic atomization on discharge electrode 311. That is, electrostatic atomization device 30 of the above-mentioned type is excellent in usability from a viewpoint that replenishment of water is unnecessary. However, as described above, when electrostatic atomization device 30 is exposed to adjusted air, there is a concern that dew condensation water cannot be produced on the discharge electrode in a stable manner.

Therefore, in the air-blowing system having discharge device of the present exemplary embodiment, electrostatic atomization device 30 is disposed outside air supply passage 260, that is, outside pipe portion 230. With such a configuration, it is possible to suppress the exposure of electrostatic atomization device 30 to adjusted high temperature air or adjusted low humidity air which flows through air supply passage 260. Accordingly, electrostatic atomization device 30 can produce charged fine water particles 40 efficiently without being affected by adjusted air which flows through air supply passage 260.

Hereinafter, electrostatic atomization device 30 of the air-blowing system having discharge device of the present exemplary embodiment and, particularly, the arrangement relationship of introducing pipe 50 is described with reference to FIG. 5.

Figure 5:
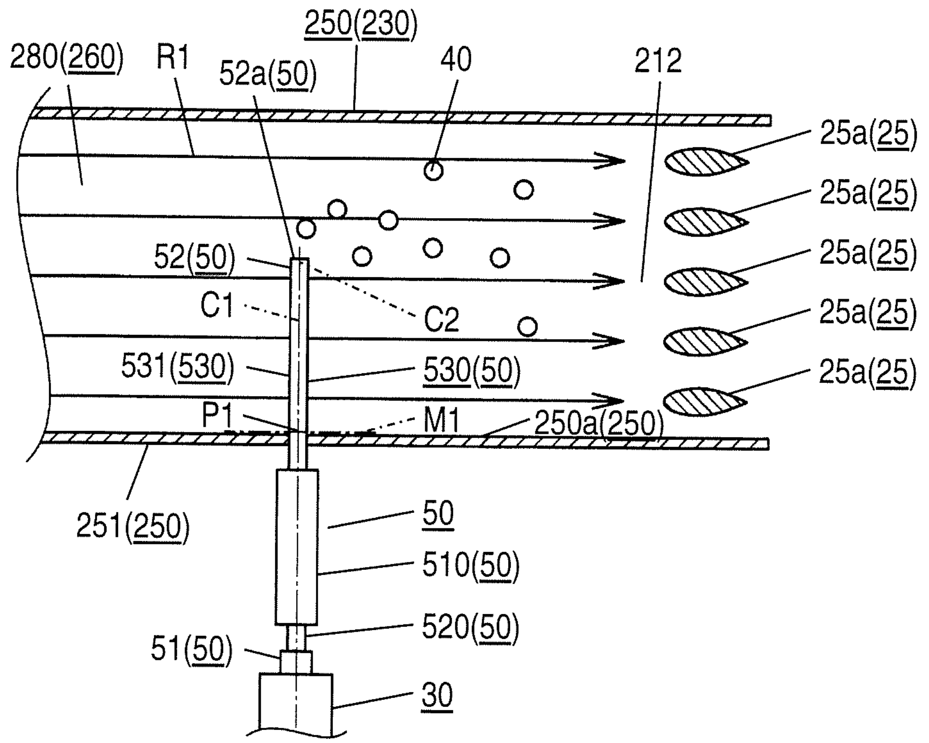
FIG. 5 is a view schematically showing a state where the discharge device according to the exemplary embodiment is disposed on the air-blowing system.

FIG. 5 is a view schematically showing one example of a state where the discharge device according to the exemplary embodiment is disposed on the air-blowing system.

As shown in FIG. 5, electrostatic atomization device 30 of the present exemplary embodiment is connected to the inside of branch passage 280 (air supply passage 260) through introducing pipe 50. To be more specific, one end 51 of introducing pipe 50 is connected to electrostatic atomization device 30 which is disposed outside one branch pipe 250, for example, which forms pipe portion 230. On the other hand, other end 52 of introducing pipe 50 is disposed in branch passage 280 (air supply passage 260) which is formed in the inside of branch pipe 250 through branch pipe 250. With such a configuration, charged fine water particles 40 generated by electrostatic atomization device 30 are introduced into branch passage 280. For example, introducing pipe 50 is formed using a resin such as polypropylene.

To be more specific, as shown in FIG. 5, introducing pipe 50 includes body portion 510, connecting portion 520, nozzle portion 530 and the like. Connecting portion 520 is continuously formed with one end side of body portion 510 and, at the same time, is connected to electrostatic atomization device 30 by way of one end 51 of introducing pipe 50. Nozzle portion 530 is continuously formed with the other end side of body portion 510 and, at the same time, a distal end portion which forms other end 52 of introducing pipe 50 is inserted into the inside of branch passage 280.

In this case, in the present exemplary embodiment, electrostatic atomization device 30, body portion 510, connecting portion 520, and nozzle portion 530 are arranged on one straight line extending in a direction orthogonal to an extending direction of branch pipe 250, for example. Accordingly, nozzle portion 530 of introducing pipe 50 is formed linearly. Opening face 52*a* is formed on a distal end portion (other end 52 of introducing pipe 50) of nozzle portion 530 disposed in the inside of branch passage 280. That is, when nozzle portion 530 is inserted into branch passage 280, introducing pipe 50 is disposed such that an other end 52 side of introducing pipe 50 protrudes toward the inside of branch passage 280 from a wall portion of branch pipe 250 which defines branch passage 280. It is not particularly necessary to arrange electrostatic atomization device 30, body portion 510, connecting portion 520, and nozzle portion 530 on a straight line.

By inserting nozzle portion 530 in branch passage 280, air in introducing pipe 50 passes through opening face 52*a*, and is introduced into branch passage 280. In this case, a distal end side (opening face 52*a* side) of nozzle portion 530 is disposed so as to protrude linearly toward the inside of branch passage 280. With such a configuration, in nozzle portion 530, protruding portion 531 which protrudes linearly toward the inside of branch passage 280 from the wall portion of branch pipe 250 which defines branch passage 280 is formed on the other end 52 side of introducing pipe 50.

Due to the above-described arrangement configuration, charged fine water particles 40 generated by electrostatic atomization device 30 can be introduced into branch passage 280 more efficiently.

To be more specific, as shown in FIG. 5, in a state where the other end 52 side of introducing pipe 50 is disposed in branch passage 280, introducing pipe 50 is disposed such that opening face 52*a* of nozzle portion 530 and a main stream direction (arrow direction) of air flow R1 which flows through branch passage 280 at a predetermined point of opening face 52*a* become substantially parallel (including parallel) to each other. Accordingly, in the present exemplary embodiment, a surface of opening face 52*a* is formed so as to extend in a direction orthogonal to center axis C1 of introducing pipe 50. That is, straight-line-shaped nozzle portion 530 is inserted in straight line portion 251 of branch pipe 250 in a state where center axis C1 of introducing pipe 50 is directed orthogonal to branch pipe 250. With such a configuration, in a state where the other end 52 side of introducing pipe 50 is disposed in branch passage 280, the surface of opening face 52*a* and the extending direction of straight line portion 251 are disposed substantially parallel (including parallel) to each other. In this case, a main stream direction of air flow R1 which flows through straight line portion 251 of branch pipe 250 agrees with the extending direction of straight line portion 251. Accordingly, opening face 52*a* of nozzle portion 530 (introducing pipe 50) and the main stream direction of air flow R1 become substantially parallel (including parallel) to each other.

When straight-line-shaped nozzle portion 530 is inserted in a direction orthogonal to the straight line portion 251 of branch pipe 250, the main stream direction of air flow R1 becomes equal at all points on the surface of opening face 52*a*. Accordingly, an arbitrary point on opening face 52*a* can be set as the predetermined point of opening face 52*a*. Therefore, in the present exemplary embodiment, center point C2 of opening face 52*a* (intersection between center axis C1 and opening face 52*a*) is set as the predetermined point of opening face 52*a*.

In this case, protruding portion 531 of introducing pipe 50 is disposed in a state where protruding portion 531 orthogonally intersects with tangential plane M1 of inner surface 250*a* of branch pipe 250 at intersection P1 between center axis C1 of protruding portion 531 and inner surface 250*a* of branch pipe 250. With such a configuration, opening face 52*a* is disposed substantially parallel (including parallel) to tangential plane M1 of branch pipe 250.

Although introducing pipe 50 can be formed using a resiliently deformable material, it is preferable that at least nozzle portion 530 be formed using a material having rigidity. With such a configuration, deformation of nozzle portion 530 disposed orthogonal to the flowing direction of air flow R1 can be prevented. As a result, it is possible to suppress the occurrence of a phenomenon that opening face 52*a* of nozzle portion 530 is displaced from a substantially parallel (including parallel) state with respect to the main stream direction of air flow R1.

As described above, introducing pipe 50 connected to electrostatic atomization device 30 is disposed in the inside of air supply passage 260 so that charged fine water particles 40 are introduced into air supply passage 260.

In vehicle-use air conditioner 20 having the above-mentioned configuration, firstly, the flow of air is generated by supplying electricity to blower 21. Accordingly, air outside cabin 3 or air inside cabin 3 is taken into air conditioning portion 220 through suction port 211 of housing 210.

Air taken into air conditioning portion 220 passes through filter 22, so that foreign substances in air are removed. Then, air from which the foreign substances are removed is introduced into evaporator 23 where a temperature or the like of air is adjusted.

Air whose temperature is adjusted by evaporator 23 (adjusted air having viscosity) is introduced into air supply passage body 270 from air conditioning portion 220. Introduced air passes through air supply passage body 270, and is introduced into one or more branched branch passages 280. Air introduced in branch passages 280 passes through branch passages 280, and is blown off into cabin 3 from air outlets 212 of housing 210 formed on a downstream side of branch passages 280.

At this stage of operation, at opening face 52*a* on the other end 52 side of introducing pipe 50 in branch passage 280, air in the inside of introducing pipe 50 and air (adjusted air having viscosity) which passes through branch passage 280 are brought into contact with each other. Accordingly, the adjusted air and the air in the inside of introducing pipe 50 are brought into contact with each other thus generating a frictional force therebetween. As a result, the air in the inside of introducing pipe 50 is pulled to the adjusted air due to a frictional force, and is induced into branch passage 280 sequentially.

As described above, opening face 52*a* of introducing pipe 50 of the present exemplary embodiment is disposed substantially parallel (including parallel) to the main stream direction of air flow R1 which flows through branch passage 280. Accordingly, on opening face 52*a*, a frictional force generated by contact between air flowing through branch passage 280 and air in introducing pipe 50 is increased. Generally, a frictional force which acts between the above-mentioned airs is increased or decreased corresponding to a flow speed of air n branch passage 280. That is, in the present exemplary embodiment, a flow speed of air which flows through a center (center portion) of branch passage 280 becomes the fastest and hence, a frictional force at such a portion also becomes maximum. Accordingly, opening face 52*a* of introducing pipe 50 is disposed at the center portion of branch passage 280. The same also goes for a second exemplary embodiment.

Further, also in third to seventh exemplary embodiments described later, a frictional force is increased at an air passage such as an inner side of a bent portion, a narrow portion and the like where a flow speed of air which flows through branch passage 280 is high, for example. Accordingly, opening face 52*a* of introducing pipe 50 is disposed in an air passage such as an inner side of a bent portion and a narrow portion where a flow speed of air is high. Detailed configuration is described later.

When the above-mentioned frictional force is increased, air in introducing pipe 50 is easily induced into the inside of branch passage 280. Accordingly, air in introducing pipe 50 is sequentially induced into branch passage 280. With such a configuration, the flow of air toward branch passage 280 from the inside of electrostatic atomization device 30 which is connected to introducing pipe 50 is easily generated. As a result, charged fine water particles 40 generated by electrostatic atomization device 30 flow into the inside of branch passage 280 more efficiently.

That is, air containing charged fine water particles 40 in introducing pipe 50 is induced and merges with adjusted air which flows through branch passage 280. Then, adjusted air containing charged fine water particles 40 passes through between air direction adjusting plates 25*a* disposed in air outlet 212, and is dispersed to the outside of vehicle-use air conditioner 20. In the case of the present exemplary embodiment, adjusted air containing charged fine water particles 40 is dispersed to the inside of cabin 3.

In the present exemplary embodiment, the description is made by taking a case where electrostatic atomization device 30 and introducing pipe 50 are disposed in one branch passage 280 out of one or more branched branch passages 280 as an example. However, the present invention is not limited to such a configuration. For example, a configuration may be adopted where electrostatic atomization device 30 and introducing pipe 50 are disposed in each of one or more branch passages 280 respectively, and adjusted air containing charged fine water particles 40 is blown off from air outlets 212 of respective branch passages 280. With such a configuration, charged fine water particles 40 generated by electrostatic atomization device 30 can be blown off from respective air outlets 212. As a result, the above-mentioned advantageous effects acquired by charged fine water particles 40 such as odor removal can be acquired within a short time.

As has been described heretofore, air-blowing system having discharge device 10 according to the present exemplary embodiment includes: air supply passage 260 having air outlets 212 from which air is blown off; and electrostatic atomization device 30 provided for generating charged fine water particles 40 which are active ingredients and disposed outside air supply passage 260. Air-blowing system having discharge device 10 includes introducing pipe 50 where one end 51 of introducing pipe 50 is connected to electrostatic atomization device 30, other end 52 of introducing pipe 50 is disposed in air supply passage 260. Charged fine water particles 40 are introduced into branch passage 280. Introducing pipe 50 has opening face 52*a* on the other end 52 side. The other end 52 side of introducing pipe 50 is arranged such that, in a state where the other end 52 side of introducing pipe 50 is disposed in branch passage 280, opening face 52*a* and the main stream direction of air flow R1 which flows through branch passage 280 at center point C2 corresponding to the predetermined point of opening face 52*a* become substantially parallel to each other.

With such a configuration, on opening face 52*a* of introducing pipe 50, a frictional force generated when air flowing through branch passage 280 and air in introducing pipe 50 are brought into contact with each other can be increased. Accordingly, air in introducing pipe 50 which is brought into contact with opening face 52*a* of introducing pipe 50 is easily induced into branch passage 280. As a result, air in introducing pipe 50 is sequentially induced into branch passage 280. Accordingly, the flow of air toward branch passage 280 from the inside of electrostatic atomization device 30 connected to introducing pipe 50 is easily generated.

That is, according to air-blowing system having discharge device 10 of the present exemplary embodiment, charged fine water particles 40 generated by electrostatic atomization device 30 which is an example of the discharge device can be made to flow into branch passage 280 more efficiently.

Further, in air-blowing system having discharge device 10 of the present exemplary embodiment, air whose temperature and humidity are adjusted by air conditioning portion 220 and having viscosity is brought into contact with air in introducing pipe 50. Accordingly, due to such a contact, a frictional force generated between both airs is further increased. With such a configuration, air in introducing pipe 50 which is brought into contact with opening face 52*a* of introducing pipe 50 is easily induced into branch passage 280.

That is, air in introducing pipe 50 is induced into branch passage 280 by making use of viscosity of air flowing through branch passage 280. With such an operation, it is unnecessary to provide an air supply portion for forcibly discharging charged fine water particles 40 to electrostatic atomization device 30 per se. As a result, configuration of air-blowing system having discharge device 10 can be simplified and, at the same time, the reduction of cost can be realized.

As a matter of course, also in the present exemplary embodiment, it is needless to say that an air supply portion such as a fan, for example, may be added to electrostatic atomization device 30 per se. However, there is a concern that addition of air the supply portion generates vibrations, noises and the like, for example. Further, there is a concern that the device becomes large-sized or a cost of the device is pushed up.

Therefore, air-blowing system having discharge device 10 of the present exemplary embodiment has the configuration where an air supply portion is not provided to electrostatic atomization device 30 per se. With such a configuration, generation of vibrations, noises and the like attributed to the air supply portion can be reduced. Further, the large-sizing of the device and the push-up of a manufacturing cost of the device can be suppressed.

Further, by inducing air in introducing pipe 50 by making use of viscosity of air described above, it is unnecessary to induce air in introducing pipe 50 by making use of a local and unstable negative pressure generated in branch passage 280 which forms air supply passage 260. Accordingly, air in introducing pipe 50 can be introduced into branch passage 280 with more certainty. In this case, it may be also adopted a configuration where air in introducing pipe 50 is introduced into branch passage 280 also by making use of negative pressure generated in branch passage 280 simultaneously.

When only a negative pressure is used, a mounting position of introducing pipe 50 is limited to a portion where a negative pressure is generated and hence, such a configuration is not favorable. Further, as shown in FIG. 5, when air direction adjusting plates 25*a* are disposed in the vicinity of air outlet 212, a portion where a negative pressure is generated is changed or disappeared depending on a position of air direction adjusting plate 25*a*. Accordingly, there is a concern that a negative pressure cannot be used and hence, such a configuration is not favorable.

On the other hand, according to air-blowing system having discharge device 10 of the present exemplary embodiment, air in introducing pipe 50 can be introduced into branch passage 280 without depending on a negative pressure generated in branch passage 280. Accordingly, a mounting position of introducing pipe 50 can be set more freely. Further, even when a negative pressure cannot be generated by being affected by air direction adjusting plates 25*a*, air in introducing pipe 50 can be introduced into branch passage 280 by making use of a frictional force with more certainty.

Further, introducing pipe 50 of air-blowing system having discharge device 10 of the present exemplary embodiment has protruding portion 531 which protrudes linearly toward the inside of branch passage 280 from the wall portion of branch pipe 250 which defines branch passage 280 on the other end 52 side of introducing pipe 50. Protruding portion 531 is disposed in a state where protruding portion 531 orthogonally intersects with tangential plane M1 of inner surface 250*a* of branch pipe 250 at intersection P1 between center axis C1 of protruding portion 531 and inner surface 250*a* of branch pipe 250. With such a configuration, it is possible to suppress the occurrence of a phenomenon that the extending direction of opening face 52*a* of introducing pipe 50 (direction along tangential plane M1) is displaced from the main stream direction of air flow R1 at center point C2 at the predetermined point of opening face 52*a*. That is, the extending direction of opening face 52*a* and the main stream direction of air flow R1 can be disposed substantially parallel to each other (including parallel) more easily.

Second Exemplary Embodiment

Hereinafter, a configuration of an air-blowing system having discharge device according to a second exemplary embodiment of the present invention, particularly, an arrangement relationship between branch pipe 250 and introducing pipe 50 of electrostatic atomization device 30 is described with reference to FIG. 6.

Figure 6:
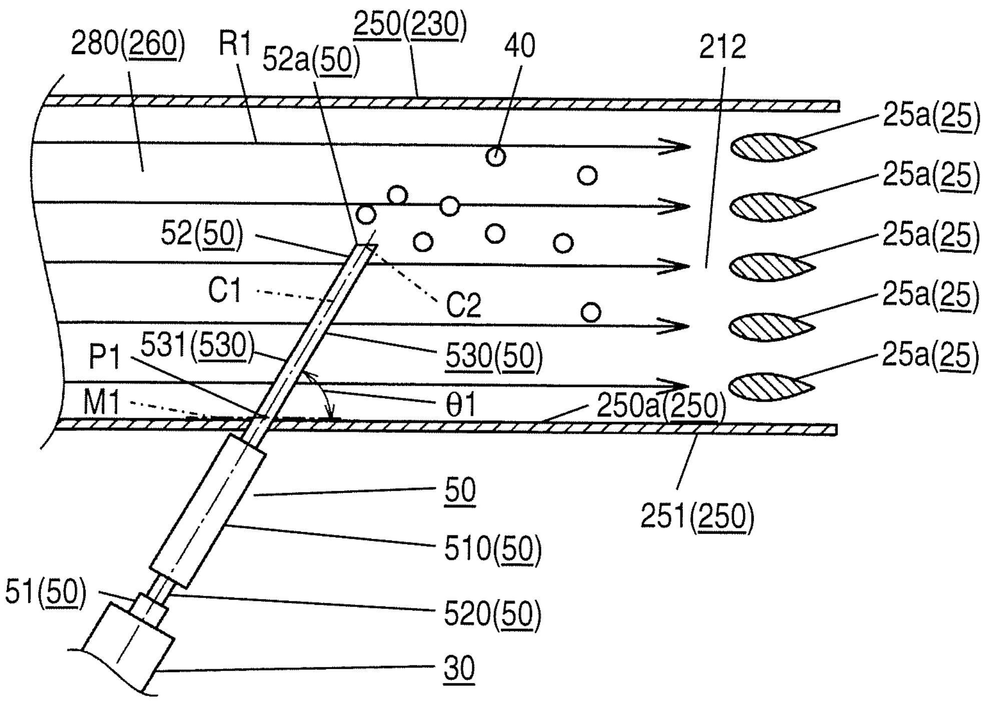
FIG. 6 is a view schematically showing a state where a discharge device according to a second exemplary embodiment of the present invention is disposed on an air-blowing system.

FIG. 6 is a view schematically showing a state where the discharge device according to the exemplary embodiment is disposed on the air-blowing system.

The air-blowing system having discharge device of the present exemplary embodiment uses electrostatic atomization device 30 as the discharge device in the same manner as the above-mentioned first exemplary embodiment. The air-blowing system having discharge device of the present exemplary embodiment is configured to blow off air containing active ingredients generated by electrostatic atomization device 30 into the inside of cabin 3 from air outlet 212 of at least one branch passage 280 out of one or more branched branch passages 280.

That is, charged fine water particles 40 which are active ingredients generated by electrostatic atomization device 30 are taken into branch passage 280. Further, the air-blowing system having discharge device is configured to blow off air containing charged fine water particles 40 into the inside of cabin 3 from air outlet 212.

To be more specific, in the same manner as the first exemplary embodiment, electrostatic atomization device 30 is disposed outside air supply passage 260. With such a configuration, it is possible to suppress the exposure of electrostatic atomization device 30 to high temperature air or low humidity air which flows through air supply passage 260.

As shown in FIG. 6, in electrostatic atomization device 30 of the present exemplary embodiment, one end 51 of introducing pipe 50 is connected to electrostatic atomization device 30 which is disposed outside one branch pipe 250 which forms pipe portion 230, for example. On the other hand, other end 52 of introducing pipe 50 is disposed in branch passage 280 (air supply passage 260). With such a configuration, charged fine water particles 40 generated by electrostatic atomization device 30 are introduced into branch passage 280.

To be more specific, introducing pipe 50 includes body portion 510, connecting portion 520, nozzle portion 530 and the like. Connecting portion 520 is continuously formed with one end side of body portion 510 and, at the same time, is connected to electrostatic atomization device 30 by way of one end 51 of introducing pipe 50. Nozzle portion 530 is continuously formed with the other end side of body portion 510 and, at the same time, a distal end portion which forms other end 52 of introducing pipe 50 is inserted into the inside of branch passage 280.

Nozzle portion 530 of introducing pipe 50 is formed linearly in the same manner as the first exemplary embodiment. Opening face 52*a* is formed on a distal end portion (other end 52 of introducing pipe 50) of nozzle portion 530 disposed in the inside of branch passage 280. Further, with respect to nozzle portion 530, protruding portion 531 which protrudes linearly toward the inside of branch passage 280 from the wall portion of branch pipe 250 defining branch passage 280 is formed on the other end 52 side of introducing pipe 50.

Also in introducing pipe 50 of the present exemplary embodiment, in a state where the other end 52 side of introducing pipe 50 is disposed in branch passage 280, introducing pipe 50 is disposed such that opening face 52*a* and a main stream direction (arrow direction) of air flow R1 which flows through branch passage 280 at a predetermined point of opening face 52*a* become substantially parallel (including parallel) to each other.

In this case, as shown in FIG. 6, introducing pipe 50 of the present exemplary embodiment is disposed such that opening face 52*a* is inclined by angle θ1 with respect to a direction orthogonal to center axis C1. That is, nozzle portion 530 of introducing pipe 50 is inserted into the inside of branch pipe 250 in a state where center axis C1 of introducing pipe 50 is inclined by angle θ1 with respect to the extending direction of straight line portion 251 of branch pipe 250.

To be more specific, nozzle portion 530 is inserted into straight line portion 251 of branch pipe 250 such that a proximal side of nozzle portion 530 (electrostatic atomization device 30 side) is disposed on an upstream side, and a distal end side (opening face 52*a* side) of nozzle portion 530 is disposed on a downstream side. With such a configuration, in a state where the other end 52 side of introducing pipe 50 is disposed in branch passage 280, opening face 52*a* of introducing pipe 50 and the extending direction of straight line portion 251 of branch pipe 250 are disposed substantially parallel (including parallel) to each other. In this case, a main stream direction of air flow R1 which flows through straight line portion 251 of branch pipe 250 agrees with the extending direction of straight line portion 251. Accordingly, opening face 52*a* of introducing pipe 50 which is inclined by angle θ1 and the main stream direction of air flow R1 become substantially parallel (including parallel) to each other.

When nozzle portion 530 is inserted in straight line portion 251 of branch pipe 250 in an inclined manner at angle θ1, main stream direction of air flow R1 becomes equal at all points on the surface of opening face 52*a*. Accordingly, an arbitrary point on opening face 52*a* can be set as the predetermined point of opening face 52*a*. Therefore, also in the present exemplary embodiment, center point C2 of opening face 52*a* (intersection between center axis C1 and opening face 52*a*) is set as the predetermined point of opening face 52*a* in the same manner as the first exemplary embodiment.

In this case, protruding portion 531 of introducing pipe 50 is disposed in a state where other end 52 of introducing pipe 50 is inclined at angle θ1 toward a downstream side with respect to tangential plane M1 of inner surface 250*a* of branch pipe 250 at intersection P1 between center axis C1 of protruding portion 531 and inner surface 250*a* of branch pipe 250. With such a configuration, opening face 52*a* is disposed substantially parallel (including parallel) to tangential plane M1 of branch pipe 250.

With such a configuration, also in the arrangement configuration of the present exemplary embodiment, it is possible to acquire substantially the same manner of operation and advantageous effects as the above-mentioned first exemplary embodiment.

Further, introducing pipe 50 of air-blowing system having discharge device 10 of the present exemplary embodiment has protruding portion 531 which protrudes linearly toward the inside of branch passage 280 from the wall portion of branch pipe 250 which defines branch passage 280 on the other end 52 side of introducing pipe 50. Protruding portion 531 is disposed in a state where other end 52 is inclined at angle θ1 toward a downstream side with respect to tangential plane M1 of inner surface 250*a* of branch pipe 250 at intersection P1 between center axis C1 of protruding portion 531 and inner surface 250*a* of branch pipe 250. With such a configuration, it is possible to suppress the occurrence of a phenomenon that the extending direction of opening face 52*a* of introducing pipe 50 (direction along tangential plane M1) is displaced from the main stream direction of air flow R1 at center point C2 at the predetermined point of opening face 52*a*. That is, the extending direction of opening face 52*a* and the main stream direction of air flow R1 can be disposed substantially parallel to each other (including parallel) more easily.

Further, in air-blowing system having discharge device 10 of the present exemplary embodiment, protruding portion 531 of introducing pipe 50 is inclined such that the other end 52 side is disposed on a downstream side. With such a configuration, the main stream direction (center axis C1 direction) of air flow passage in introducing pipe 50 can be made to approach the main stream direction of air flow R1 in branch passage 280. Accordingly, air in introducing pipe 50 can be introduced into the inside of branch passage 280 by inducing by air flowing through branch passage 280 more smoothly.

Third Exemplary Embodiment

Hereinafter, a configuration of an air-blowing system having discharge device according to a third exemplary embodiment of the present invention, particularly, an arrangement relationship between branch pipe 250 and introducing pipe 50 of electrostatic atomization device 30 is described with reference to FIG. 7.

Figure 7:
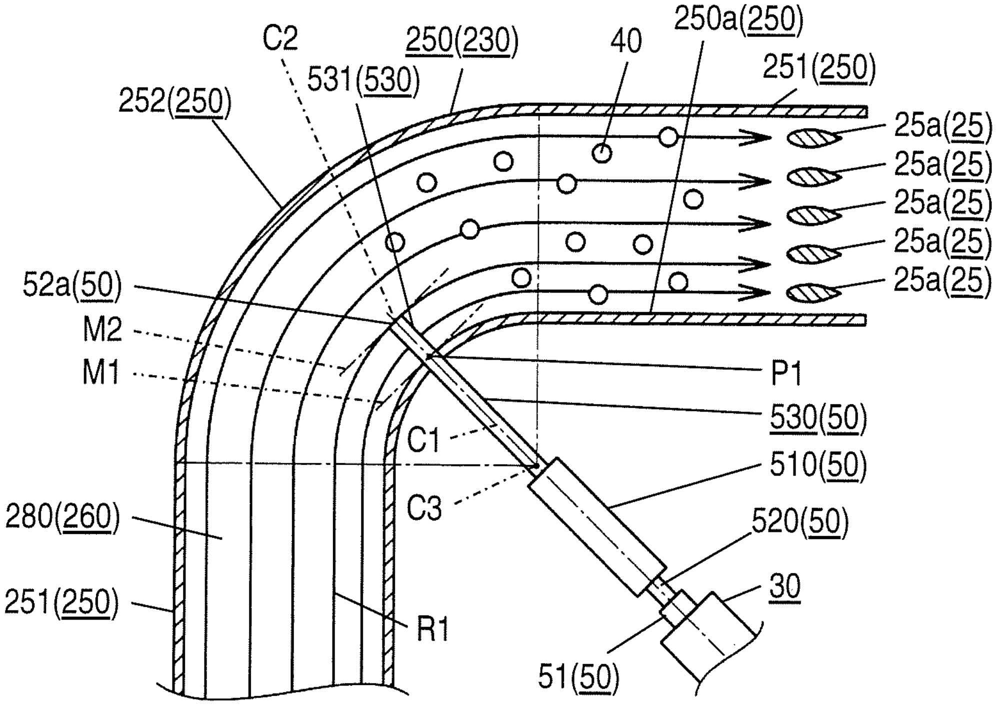
FIG. 7 is a view schematically showing a state where a discharge device according to a third exemplary embodiment of the present invention is disposed on an air-blowing system.

FIG. 7 is a view schematically showing a state where the discharge device according to the exemplary embodiment is disposed on the air-blowing system.

Here, the air-blowing system having discharge device of the present exemplary embodiment uses electrostatic atomization device 30 as the discharge device in the same manner as the above-mentioned first and second exemplary embodiments. Further, the air-blowing system having discharge device of the present exemplary embodiment is configured to blow off air containing active ingredients generated by electrostatic atomization device 30 into the inside of cabin 3 from air outlet 212 of at least one branch passage 280 out of one or more branched branch passages 280.

That is, charged fine water particles 40 which are active ingredients generated by electrostatic atomization device 30 are taken into branch passage 280. Further, the air-blowing system having discharge device is configured to blow off air containing charged fine water particles 40 into the inside of cabin 3 from air outlet 212.

To be more specific, in the same manner as the above-mentioned respective exemplary embodiments, electrostatic atomization device 30 is disposed outside air supply passage 260. With such a configuration, it is possible to suppress the exposure of electrostatic atomization device 30 to high temperature air or low humidity air which flows through air supply passage 260.

As shown in FIG. 7, in electrostatic atomization device 30 of the present exemplary embodiment, one end 51 of introducing pipe 50 is connected to electrostatic atomization device 30 which is disposed outside one branch pipe 250 which forms pipe portion 230, for example. On the other hand, other end 52 of introducing pipe 50 is disposed in branch passage 280 (air supply passage 260). With such a configuration, charged fine water particles 40 generated by electrostatic atomization device 30 are introduced into branch passage 280.

To be more specific, introducing pipe 50 includes body portion 510, connecting portion 520, nozzle portion 530 and the like. Connecting portion 520 is continuously formed with one end side of body portion 510 and, at the same time, is connected to electrostatic atomization device 30 by way of one end 51 of introducing pipe 50. Nozzle portion 530 is continuously formed with the other end side of body portion 510 and, at the same time, a distal end portion which forms other end 52 of introducing pipe 50 is inserted into the inside of branch passage 280.

In this case, nozzle portion 530 of introducing pipe 50 is formed linearly in the same manner as the above-mentioned respective exemplary embodiments. Opening face 52*a* is formed on a distal end portion (other end 52 of introducing pipe 50) of nozzle portion 530 disposed in the inside of branch passage 280. Further, with respect to nozzle portion 530, protruding portion 531 which protrudes linearly toward the inside of branch passage 280 from the wall portion of branch pipe 250 defining branch passage 280 is formed on an other end 52 side of introducing pipe 50.

Also in introducing pipe 50 of the present exemplary embodiment, in a state where the other end 52 side of introducing pipe 50 is disposed in branch passage 280, introducing pipe 50 is disposed such that opening face 52*a* and a main stream direction (arrow direction) of air flow R1 which flows through branch passage 280 at center point C2

(predetermined point) of opening face 52*a* become substantially parallel (including parallel) to each other.

In this case, as shown in FIG. 7, branch pipe 250 of the present exemplary embodiment is formed into a bent shape. To be more specific, branch pipe 250 includes straight line portion 251 extending in one direction, straight line portion 251 extending in a direction orthogonal to one direction, and bent portion 252 which smoothly connects straight line portions 251, 252 to each other. Bent portion 252 of branch pipe 250 has inner and outer wall portions formed concentrically with center C3 of introducing pipe 50.

Further, introducing pipe 50 of the present exemplary embodiment has opening face 52*a* formed in an extending manner in a direction orthogonal to center axis C1 in the same manner as the above-mentioned respective exemplary embodiments. Nozzle portion 530 is inserted into bent portion 252 of branch pipe 250. In this case, protruding portion 531 is disposed such that center axis C1 orthogonally intersects with tangential plane M1 of inner surface 250*a* at intersection P1 between center axis C1 of protruding portion 531 and inner surface 250*a* of branch pipe 250. With such a configuration, in a state where the other end 52 side of introducing pipe 50 is disposed in branch passage 280, opening face 52*a* of introducing pipe 50 is disposed substantially parallel (including parallel) to tangential plane M1.

That is, protruding portion 531 is disposed in a state where protruding portion 531 orthogonally intersects with tangential plane M1 of inner surface 250*a* at intersection P1 between center axis C1 of protruding portion 531 and inner surface 250*a* of branch pipe 250. With such a configuration, opening face 52*a* is disposed substantially parallel (including parallel) to tangential plane M1 of branch pipe 250.

In this case, a main stream direction of air flow R1 which flows through bent portion 252 of branch pipe 250 is bent along bent portion 252. Accordingly, the main stream direction of air flow R1 which flows through branch passage 280 at center point C2 (intersection between center axis C1 and opening face 52*a*) of opening face 52*a* becomes a tangential direction at center point C2 of air flow R1 which flows on center point C2.

The tangent line is a line included in tangential plane M2 at center point C2 of air flow R1 which flows on center point C2 of opening face 52*a*. Accordingly, opening face 52*a* and tangential plane M2 become substantially parallel (including parallel) to each other. That is, as shown in FIG. 7, by inserting nozzle portion 530 in bent portion 252 of branch pipe 250, opening face 52*a* and the main stream direction of air flow R1 which flows through branch passage 280 at a predetermined point of opening face 52*a* are disposed substantially parallel (including parallel) to each other.

With such a configuration, also in the arrangement configuration of the present exemplary embodiment, it is possible to acquire substantially the same manner of operation and advantageous effects as the above-mentioned respective exemplary embodiments.

Further, the predetermined point of introducing pipe 50 of air-blowing system having discharge device 10 according to the present exemplary embodiment is set as center point C2 of opening face 52*a*. Accordingly, also when air flow R1 flows through air supply passage 260 in a bending manner, opening face 52*a* can be disposed substantially along the main stream direction of air flow R1 as a whole.

On the other hand, in a case where the predetermined point is set to an upstream end side of opening face 52*a*, when air flow R1 flows in a bending manner, the main stream direction of actual air flow R1 and the extending direction of opening face 52*a* are separated from each other at a downstream end of opening face 52*a*. Accordingly, the whole surface of opening face 52*a* is not disposed along the main stream direction of air flow R1. In the same manner, also when the predetermined point is set at a downstream end side of opening face 52*a*, the whole surface of opening face 52*a* cannot be disposed along the main stream direction of air flow R1.

Therefore, in the present exemplary embodiment, the predetermined point is set as center point C2 of opening face 52*a*. With such a configuration, a separation amount between the extending direction of opening face 52*a* and the main stream direction of actual air flow R1 at an upstream end and a downstream end of opening face 52*a* can be made relatively small. That is, also when air flow R1 which flows through air supply passage 260 is bent, a surface of opening face 52*a* can be disposed substantially along the main stream direction of air flow R1 as a whole. With such a configuration, a frictional force between air flowing through air supply passage 260 and air in introducing pipe 50 is further increased at respective points on the surface of opening face 52*a*. As a result, charged fine water particles 40 generated by electrostatic atomization device 30 can be made to flow into air supply passage 260 more efficiently.

Fourth Exemplary Embodiment

Hereinafter, a configuration of an air-blowing system having discharge device according to a fourth exemplary embodiment of the present invention, particularly, an arrangement relationship between branch pipe 250 and introducing pipe 50 of electrostatic atomization device 30 is described with reference to FIG. 8.

Figure 8:
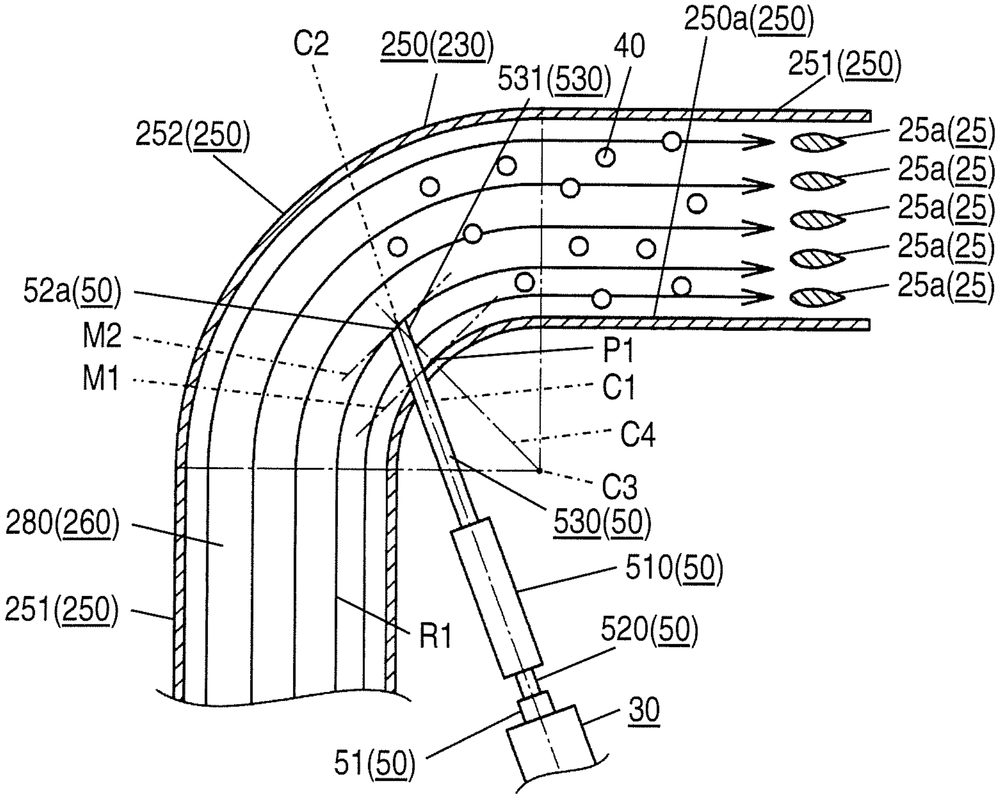
FIG. 8 is a view schematically showing a state where a discharge device according to a fourth exemplary embodiment of the present invention is disposed on an air-blowing system.

FIG. 8 is a view schematically showing a state where the discharge device according to the exemplary embodiment is disposed on the air-blowing system.

Here, the air-blowing system having discharge device of the fourth exemplary embodiment uses electrostatic atomization device 30 as the discharge device in the same manner as the above-mentioned respective exemplary embodiments. Further, the air-blowing system having discharge device of the present exemplary embodiment is configured to blow off air containing active ingredients generated by electrostatic atomization device 30 into the inside of cabin 3 from air outlet 212 of at least one branch passage 280 out of one or more branched branch passages 280.

That is, charged fine water particles 40 which are active ingredients generated by electrostatic atomization device 30 are taken into branch passage 280. Further, the air-blowing system having discharge device is configured to blow off air containing charged fine water particles 40 into the inside of cabin 3 from air outlet 212.

To be more specific, in the same manner as the above-mentioned respective exemplary embodiments, electrostatic atomization device 30 is disposed outside air supply passage 260. With such a configuration, it is possible to suppress the exposure of electrostatic atomization device 30 to high temperature air or low humidity air which flows through air supply passage 260.

As shown in FIG. 8, in electrostatic atomization device 30 of the present exemplary embodiment, one end 51 of introducing pipe 50 is connected to electrostatic atomization device 30 which is disposed outside one branch pipe 250 which forms pipe portion 230, for example. On the other hand, other end 52 of introducing pipe 50 is disposed in branch passage 280 (air supply passage 260). With such a configuration, charged fine water particles 40 generated by electrostatic atomization device 30 are introduced into branch passage 280.

To be more specific, introducing pipe 50 includes body portion 510, connecting portion 520, nozzle portion 530 and the like. Connecting portion 520 is continuously formed with one end side of body portion 510 and, at the same time, is connected to electrostatic atomization device 30 by way of one end 51 of introducing pipe 50. Nozzle portion 530 is continuously formed with the other end side of body portion 510 and, at the same time, a distal end portion which forms other end 52 of introducing pipe 50 is inserted into the inside of branch passage 280.

In this case, nozzle portion 530 of introducing pipe 50 is formed linearly in the same manner as the above-mentioned respective exemplary embodiments. Opening face 52*a* is formed on a distal end portion (other end 52 of introducing pipe 50) of nozzle portion 530 disposed in the inside of branch passage 280. Further, with respect to nozzle portion 530, protruding portion 531 which protrudes linearly toward the inside of branch passage 280 from the wall portion of branch pipe 250 defining branch passage 280 is formed on an other end 52 side of introducing pipe 50.

Also in introducing pipe 50 of the present exemplary embodiment, in a state where the other end 52 side of introducing pipe 50 is disposed in branch passage 280, introducing pipe 50 is disposed such that opening face 52*a* and a main stream direction (arrow direction) of air flow R1 which flows through branch passage 280 at center point C2 (predetermined point) of opening face 52*a* become substantially parallel (including parallel) to each other.

To be more specific, as shown in FIG. 8, branch passage 280 of the present exemplary embodiment is formed into a bent shape in the same manner as the third exemplary embodiment. That is, branch pipe 250 includes straight line portion 251 extending in one direction, straight line portion 251 extending in a direction orthogonal to one direction, and bent portion 252 which smoothly connects straight line portions 251, 252 to each other. Bent portion 252 of branch pipe 250 has inner and outer wall portions formed concentrically with center C3 of introducing pipe 50.

Further, introducing pipe 50 of the present exemplary embodiment is disposed such that the extending direction of opening face 52*a* is inclined with respect to a direction orthogonal to center axis C1 in the same manner as the second exemplary embodiment. That is, nozzle portion 530 is inserted into the inside of branch pipe 250 in a state where nozzle portion 530 is inclined in a direction different from straight line C4 extending in a radial direction toward bent portion 252 of branch pipe 250 from center C3. Here, a state where nozzle portion 530 is inserted into bent portion 252 of branch pipe 250 in an inclined manner means that in a state where the other end 52 side of introducing pipe 50 is disposed in branch passage 280, center axis C1 of protruding portion 531 is inclined with respect to straight line C4 which connects center point C2 of opening face 52*a* and center C3 to each other.

Nozzle portion 530 may be inserted into branch pipe 250 in an inclined manner not from bent portion 252 of branch pipe 250 but from straight line portion 251 of branch pipe 250. Also in this case, it is preferable that opening face 52*a* of introducing pipe 50 (nozzle portion 530) be inserted so as to be disposed in the inside of bent portion 252 of branch pipe 250.

In this case, in the extending direction, opening face 52*a* of introducing pipe 50 is formed in an inclined manner with respect to the direction orthogonal to center axis C1 of nozzle portion 530. Further, nozzle portion 530 is inserted into bent portion 252 of branch pipe 250 in an inclined manner. With such a configuration, opening face 52*a* of introducing pipe 50 is disposed such that tangential plane M2 at center point C2 of air flow R1 which flows on center point C2 of opening face 52*a* becomes substantially parallel (including parallel) to air flow R1.

That is, introducing pipe 50 is disposed such that opening face 52*a* of introducing pipe 50 and the main stream direction of air flow R1 which flows through branch passage 280 at center point C2 (predetermined point) of opening face 52*a* become substantially parallel (including parallel) to each other. With such a configuration, in a state where the other end 52 side of introducing pipe 50 is disposed in branch passage 280, opening face 52*a* becomes substantially parallel (including parallel) to tangential plane M1 of inner surface 250*a* at intersection P1 between straight line C4 which connects center point C2 of opening face 52*a* and center C3 to each other and inner surface 250*a* of branch pipe 250.

In this case, in the same manner as the second exemplary embodiment, nozzle portion 530 is inserted into bent portion 252 of branch pipe 250 in a state where a proximal side of nozzle portion 530 (electrostatic atomization device 30 side) is disposed on an upstream side, and a distal end side (opening face 52*a* side) of nozzle portion 530 is disposed on a downstream side.

With such a configuration, also in the arrangement configuration of the present exemplary embodiment, it is possible to acquire substantially the same manner of operation and advantageous effects as the above-mentioned respective exemplary embodiments.

Fifth Exemplary Embodiment

Hereinafter, a configuration of an air-blowing system having discharge device according to a fifth exemplary embodiment of the present invention, particularly, an arrangement relationship between branch pipe 250 and introducing pipe 50 of electrostatic atomization device 30 is described with reference to FIG. 9.

Figure 9:
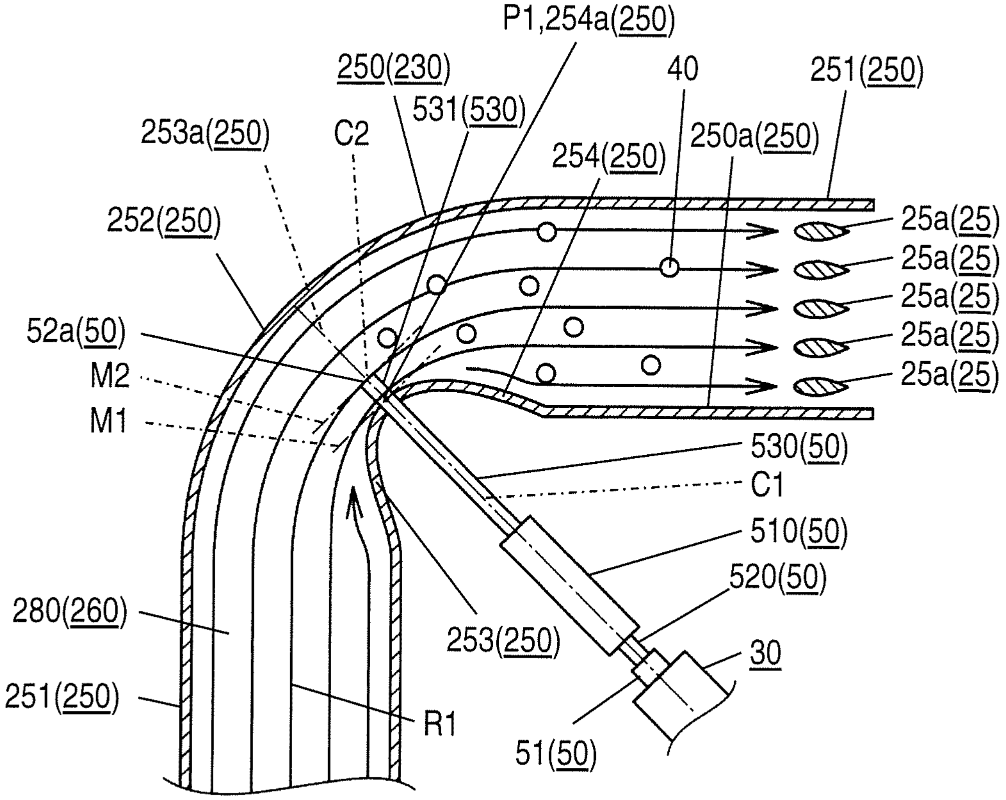
FIG. 9 is a view schematically showing a state where a discharge device according to a fifth exemplary embodiment of the present invention is disposed on an air-blowing system.

FIG. 9 is a view schematically showing a state where the discharge device according to the exemplary embodiment is disposed on the air-blowing system.

The air-blowing system having discharge device of the present exemplary embodiment uses electrostatic atomization device 30 as the discharge device in the same manner as the above-mentioned respective exemplary embodiments. Further, the air-blowing system having discharge device of the present exemplary embodiment is configured to blow off air containing active ingredients generated by electrostatic atomization device 30 into the inside of cabin 3 from air outlet 212 of at least one branch passage 280 out of one or a plurality of branched branch passages 280.

That is, charged fine water particles 40 which are active ingredients generated by electrostatic atomization device 30 are taken into branch passage 280. Further, the air-blowing system having discharge device is configured to blow off air containing charged fine water particles 40 into the inside of cabin 3 from air outlet 212.

To be more specific, in the same manner as the respective exemplary embodiments, electrostatic atomization device 30 is disposed outside air supply passage 260. With such a configuration, it is possible to suppress the exposure of electrostatic atomization device 30 to high temperature air or low humidity air which flows through air supply passage 260.

As shown in FIG. 9, in electrostatic atomization device 30 of the present exemplary embodiment, one end 51 of introducing pipe 50 is connected to electrostatic atomization device 30 which is disposed outside one branch pipe 250 which forms pipe portion 230, for example. On the other hand, other end 52 of introducing pipe 50 is disposed in branch passage 280 (air supply passage 260). With such a configuration, charged fine water particles 40 generated by electrostatic atomization device 30 are introduced into branch passage 280.

To be more specific, introducing pipe 50 includes body portion 510, connecting portion 520, nozzle portion 530 and the like. Connecting portion 520 is continuously formed with one end side of body portion 510 and, at the same time, is connected to electrostatic atomization device 30 by way of one end 51 of introducing pipe 50. Nozzle portion 530 is continuously formed with the other end side of body portion 510 and, at the same time, a distal end portion which forms other end 52 of introducing pipe 50 is inserted into the inside of branch passage 280.

In this case, nozzle portion 530 of introducing pipe 50 is formed linearly in the same manner as the above-mentioned respective exemplary embodiments. Opening face 52*a* is formed on a distal end portion (other end 52 of introducing pipe 50) of nozzle portion 530 disposed in the inside of branch passage 280. Further, with respect to nozzle portion 530, protruding portion 531 which protrudes linearly toward the inside of branch passage 280 from the wall portion of branch pipe 250 defining branch passage 280 is formed on an other end 52 side of introducing pipe 50.

Also in introducing pipe 50 of the present exemplary embodiment, in a state where the other end 52 side of introducing pipe 50 is disposed in branch passage 280, introducing pipe 50 is disposed such that opening face 52*a* and a main stream direction (arrow direction) of air flow R1 which flows through branch passage 280 at center point C2 (predetermined point) of opening face 52*a* become substantially parallel (including parallel) to each other.

As shown in FIG. 9, branch passage 280 of the present exemplary embodiment is formed into a bent shape in the same manner as the third exemplary embodiment. To be more specific, branch pipe 250 includes straight line portion 251 extending in one direction, straight line portion 251 extending in a direction orthogonal to one direction, and bent portion 252 which smoothly connects straight line portions 251, 252 to each other.

Further, bent portion 252 of branch pipe 250 of the present exemplary embodiment has narrow portion 253 where a flow passage cross-sectional area taken along a plane orthogonal to the main stream direction of air flow R1 is decreased. To be more specific, protruding portion 254 which protrudes from an inner wall portion of bent portion 252 shown in the third exemplary embodiment outward (toward a branch passage 280 side) is formed on the inner wall portion of bent portion 252. With such a configuration, narrow portion 253 is formed on bent portion 252.

In such a configuration, narrow portion 253 is formed such that a flow passage cross-sectional area of branch passage 280 is gradually decreased in a curved shape as narrow portion 253 extends toward top portion 254*a* of protruding portion 254 from an upstream side. The flow passage cross-sectional area of branch passage 280 at narrow portion 253 becomes the minimum at top portion 254*a* of protruding portion 254. Subsequently, narrow portion 253 is formed such that flow passage cross-sectional area of narrow portion 253 is gradually increased in a curved shape as narrow portion 253 extends toward a downstream side from top portion 254*a* of protruding portion 254. Finally, the flow passage cross-sectional area of narrow portion 253 becomes equal to the flow passage cross-sectional area of straight line portion 251.

That is, branch pipe 250 of the present exemplary embodiment has narrow portion 253 having minimum portion 253*a* at which the flow passage cross-sectional area becomes the minimum in bent portion 252. In the above-mentioned respective exemplary embodiments, different from branch pipe 250 of the present exemplary embodiment, branch passage 280 having substantially fixed flow passage cross-sectional area taken along a plane orthogonal to the main stream direction of air flow R1 is exemplified.

Introducing pipe 50 of the present exemplary embodiment has opening face 52*a* formed in an extending manner in a direction orthogonal to center axis C1 in the same manner as the first and third exemplary embodiments. Nozzle portion 530 is inserted into narrow portion 253 of branch pipe 250. In such a configuration, nozzle portion 530 is disposed such that intersection P1 between center axis C1 of protruding portion 531 and inner surface 250*a* of branch pipe 250 becomes top portion 254*a* of protruding portion 254.

Further, protruding portion 531 is disposed such that center axis C1 orthogonally intersects with tangential plane M1 of inner surface 250*a* at intersection P1 between center axis C1 of protruding portion 531 and inner surface 250*a* of branch pipe 250. In this case, opening face 52*a* of introducing pipe 50 is formed so as to intersect with center axis C1. Accordingly, when nozzle portion 530 is inserted into branch pipe 250 from top portion 254*a* of protruding portion 254, opening face 52*a* and tangential plane M2 at center point C2 of air flow R1 which flows on center point C2 are disposed substantially parallel (including parallel) to each other. That is, introducing pipe 50 is disposed such that opening face 52*a* of introducing pipe 50 and the main stream direction (arrow direction) of air flow R1 which flows through branch passage 280 at center point C2 (predetermined point) of opening face 52*a* become substantially parallel (including parallel) to each other. With such a configuration, opening face 52*a* is disposed substantially parallel (including parallel) to tangential plane M1 of inner surface 250*a* at intersection P1 between center axis C1 of protruding portion 531 and inner surface 250*a* of branch pipe 250.

As described above, also in the arrangement configuration of the present exemplary embodiment, it is possible to acquire substantially the same manner of operation and advantageous effects as the above-mentioned respective exemplary embodiments.

That is, air-blowing system having discharge device 10 of the present exemplary embodiment has narrow portion 253 in air supply passage 260 where a flow passage cross-sectional area taken along a plane orthogonal to the main stream direction of air flow R1 is small. Further, air-blowing system having discharge device 10 is configured such that opening face 52*a* of introducing pipe 50 is disposed in narrow portion 253.

With such a configuration, opening face 52*a* of introducing pipe 50 is disposed in a region where a flow speed of air becomes relatively fast in air supply passage 260. Accordingly, on opening face 52*a* of introducing pipe 50, a frictional force generated by contact between air flowing through air supply passage 260 and air in introducing pipe 50 is further increased. As a result, a larger amount of charged fine water particles 40 generated by electrostatic atomization device 30 can be induced and are made to flow into air supply passage 260 more efficiently.

Narrow portion 253 of the present exemplary embodiment has minimum portion 253*a* having the minimum flow passage cross-sectional area. Opening face 52*a* of introducing pipe 50 is disposed in minimum portion 253*a* of narrow portion 253. With such a configuration, opening face 52*a* is disposed in a region where a flow speed of air becomes the fastest in air supply passage 260. Accordingly, on opening face 52*a* of introducing pipe 50, a frictional force generated by contact between air flowing through air supply passage 260 and air in introducing pipe 50 is further increased. As a result, a larger amount of charged fine water particles 40 generated by electrostatic atomization device 30 can be induced and are made to flow into air supply passage 260 more efficiently.

In the present exemplary embodiment, the description is made by taking a case where center axis C1 of introducing pipe 50 is disposed so as to orthogonally intersect with tangential plane M1 of inner surface 250*a* of branch pipe 250 as an example. However, the present invention is not limited to such a configuration. For example, in the same manner as the second and fourth exemplary embodiments, a configuration may be adopted where nozzle portion 530 is inserted into branch pipe 250 in an inclined manner such that a proximal side of nozzle portion 530 of introducing pipe 50 is disposed on an upstream side, and a distal end side (opening face 52*a* side) of nozzle portion 530 is disposed on a downstream side. Accordingly, a similar or identical advantageous effects can be achieved.

Sixth Exemplary Embodiment

Hereinafter, a configuration of an air-blowing system having discharge device according to a sixth exemplary embodiment of the present invention, particularly, an arrangement relationship between branch pipe 250 and introducing pipe 50 of electrostatic atomization device 30 is described with reference to FIG. 10.

Figure 10:
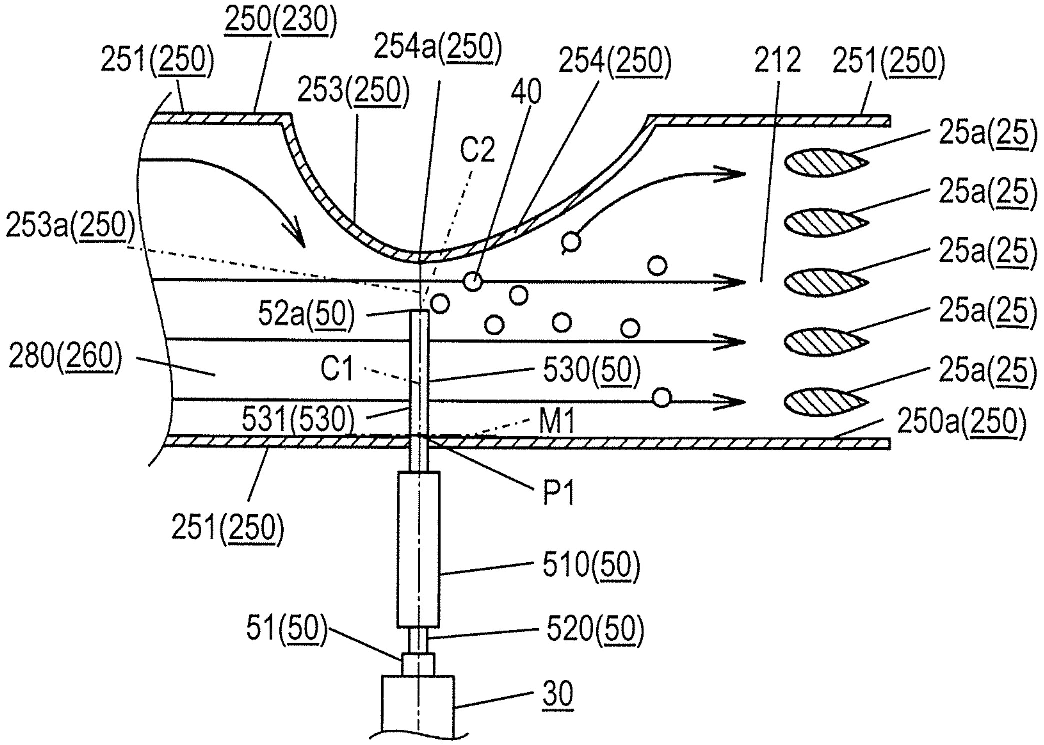
FIG. 10 is a view schematically showing a state where a discharge device according to a sixth exemplary embodiment of the present invention is disposed on an air-blowing system.

FIG. 10 is a view schematically showing a state where the discharge device according to the exemplary embodiment is disposed on the air-blowing system.

The air-blowing system having discharge device of the sixth exemplary embodiment uses electrostatic atomization device 30 as the discharge device in the same manner as the above-mentioned respective exemplary embodiments.

Further, the air-blowing system having discharge device of the present exemplary embodiment is configured to blow off air containing active ingredients generated by electrostatic atomization device 30 into the inside of cabin 3 from air outlet 212 of at least one branch passage 280 out of one or more branched branch passages 280.

That is, charged fine water particles 40 which are active ingredients generated by electrostatic atomization device 30 are taken into branch passage 280. Further, the air-blowing system having discharge device is configured to blow off air containing charged fine water particles 40 into the inside of cabin 3 from air outlet 212.

To be more specific, in the same manner as the above-mentioned respective exemplary embodiments, electrostatic atomization device 30 is disposed outside air supply passage 260. With such a configuration, it is possible to suppress the exposure of electrostatic atomization device 30 to high temperature air or low humidity air which flows through air supply passage 260.

As shown in FIG. 10, in electrostatic atomization device 30 of the present exemplary embodiment, one end 51 of introducing pipe 50 is connected to electrostatic atomization device 30 which is disposed outside one branch pipe 250 which forms pipe portion 230, for example. On the other hand, other end 52 of introducing pipe 50 is disposed in branch passage 280 (air supply passage 260). With such a configuration, charged fine water particles 40 generated by electrostatic atomization device 30 are introduced into branch passage 280.

To be more specific, introducing pipe 50 includes body portion 510, connecting portion 520, nozzle portion 530 and the like. Connecting portion 520 is continuously formed with one end side of body portion 510 and, at the same time, is connected to electrostatic atomization device 30 by way of one end 51 of introducing pipe 50. Nozzle portion 530 is continuously formed with the other end side of body portion 510 and, at the same time, a distal end portion which forms other end 52 of introducing pipe 50 is inserted into the inside of branch passage 280.

In this case, nozzle portion 530 of introducing pipe 50 is formed linearly in the same manner as the above-mentioned respective exemplary embodiments. Opening face 52*a* is formed on a distal end portion (other end 52 of introducing pipe 50) of nozzle portion 530 disposed in the inside of branch passage 280. Further, with respect to nozzle portion 530, protruding portion 531 which protrudes linearly toward the inside of branch passage 280 from the wall portion of branch pipe 250 defining branch passage 280 is formed on an other end 52 side of introducing pipe 50.

Also in introducing pipe 50 of the present exemplary embodiment, in a state where the other end 52 side of introducing pipe 50 is disposed in branch passage 280, introducing pipe 50 is disposed such that opening face 52*a* and a main stream direction (arrow direction) of air flow R1 which flows through branch passage 280 at center point C2 (predetermined point) of opening face 52*a* become substantially parallel (including parallel) to each other.

Further, as shown in FIG. 10, branch pipe 250 of the present exemplary embodiment includes narrow portion 253 on straight line portion 251 of branch pipe 250 extending linearly. Narrow portion 253 is formed such that a flow passage cross-sectional area taken along a plane orthogonal to the main stream direction of air flow R1 is gradually decreased. To be more specific, protruding portion 254 which protrudes toward a branch passage 280 side is formed on a wall portion of straight line portion 251 on one side (on a side opposite to a side where introducing pipe 50 is inserted). With such a configuration, narrow portion 253 is formed in straight line portion 251 of branch pipe 250.

In this case, narrow portion 253 is formed such that a flow passage cross-sectional area of branch passage 280 is gradually decreased in a curved shape as narrow portion 253 extends toward top portion 254*a* of protruding portion 254 from an upstream side. Further, a flow passage cross-sectional area of branch passage 280 at narrow portion 253 becomes the minimum at top portion 254*a* of protruding portion 254. Thereafter, narrow portion 253 is formed such that flow passage cross-sectional area of narrow portion 253 is gradually increased in a curved shape as narrow portion 253 extends toward a downstream side from top portion 254*a* of protruding portion 254. Finally, a flow passage cross-sectional area of narrow portion 253 becomes equal to a flow passage cross-sectional area of usual straight line portion 251.

That is, branch pipe 250 of the present exemplary embodiment has narrow portion 253 having minimum portion 253*a* at which a flow passage cross-sectional area becomes the minimum.

Further, introducing pipe 50 of the present exemplary embodiment has opening face 52*a* formed in an extending manner in a direction orthogonal to center axis C1 in the same manner as the above-mentioned first exemplary embodiment. Further, nozzle portion 530 is inserted into straight line portion 251 of branch pipe 250. In this case, protruding portion 531 is disposed such that center axis C1 orthogonally intersects with tangential plane M1 of inner surface 250*a* at intersection P1 between center axis C1 of protruding portion 531 and inner surface 250*a* of branch pipe 250. With such a configuration, in a state where the other end 52 side of introducing pipe 50 is disposed in branch passage 280, opening face 52*a* of introducing pipe 50 is disposed substantially parallel (including parallel) to tangential plane M1. That is, protruding portion 531 of nozzle portion 530 is disposed in a state where protruding portion 531 orthogonally intersects with tangential plane M1 of inner surface 250*a* at intersection P1 between center axis C1 of protruding portion 531 and inner surface 250*a* of branch pipe 250. With such a configuration, opening face 52*a* of introducing pipe 50 and tangential plane M1 are disposed substantially parallel (including parallel) to each other.

Further, in introducing pipe 50 of the present exemplary embodiment, opening face 52*a* is disposed in the inside of minimum portion 253*a*.

That is, also in the arrangement configuration of the present exemplary embodiment, it is possible to acquire substantially the same manner of operation and advantageous effects as the above-mentioned respective exemplary embodiments.

In the present exemplary embodiment, the description is made by taking a case where center axis C1 of introducing pipe 50 is disposed so as to orthogonally intersect with tangential plane M1 of inner surface 250*a* of branch pipe 250 as an example. However, the present invention is not limited to such a configuration. For example, in the same manner as the second and fourth exemplary embodiments, a configuration may be adopted where nozzle portion 530 is inserted into branch pipe 250 in an inclined manner such that a proximal side of nozzle portion 530 of introducing pipe 50 is disposed on an upstream side, and a distal end side (opening face 52*a* side) of nozzle portion 530 is disposed on a downstream side. Accordingly, a similar or identical advantageous effects can be achieved.

Seventh Exemplary Embodiment

Hereinafter, a configuration of an air-blowing system having discharge device according to a seventh exemplary embodiment of the present invention, particularly, an arrangement relationship between branch pipe 250 and introducing pipe 50 of electrostatic atomization device 30 is described with reference to FIG. 11.

Figure 11:
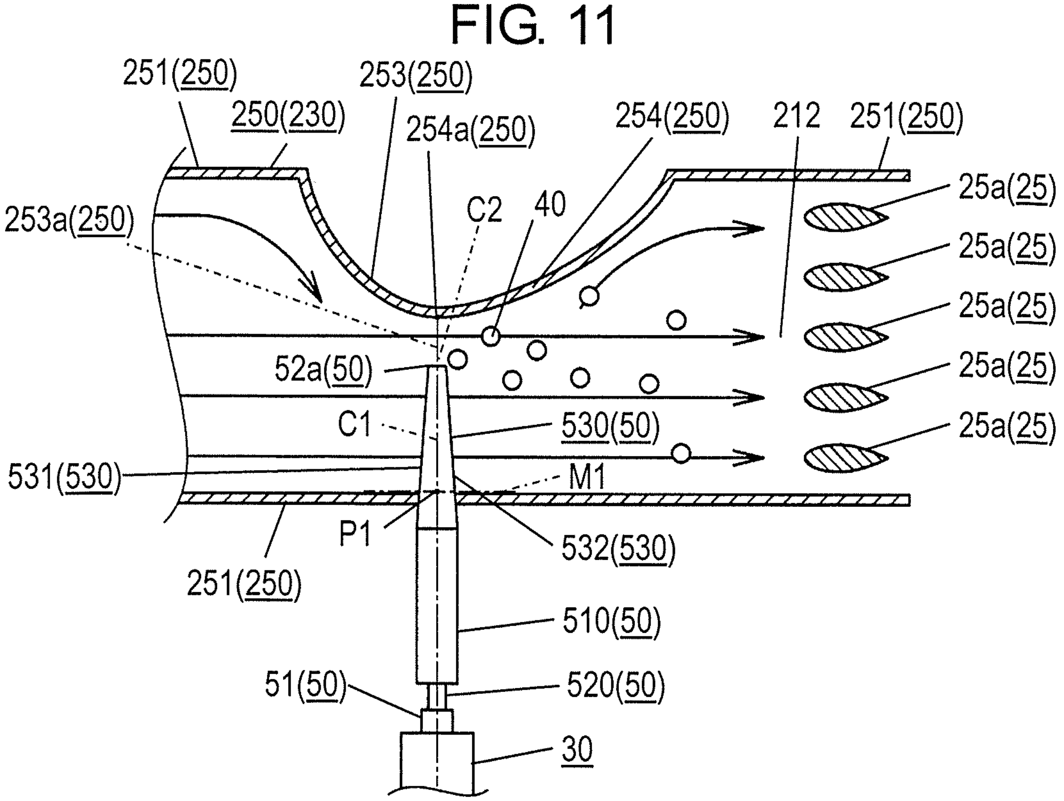
FIG. 11 is a view schematically showing a state where a discharge device according to a seventh exemplary embodiment of the present invention is disposed on an air-blowing system.

FIG. 11 is a view schematically showing a state where the discharge device according to the exemplary embodiment is disposed on the air-blowing system.

The air-blowing system having discharge device of the seventh exemplary embodiment uses electrostatic atomization device 30 as the discharge device in the same manner as the above-mentioned sixth exemplary embodiment. Further, the air-blowing system having discharge device of the present exemplary embodiment is configured to blow off air containing active ingredients generated by electrostatic atomization device 30 into the inside of cabin 3 from air outlet 212 of at least one branch passage 280 out of one or more branched branch passages 280.

That is, charged fine water particles 40 which are active ingredients generated by electrostatic atomization device 30 are taken into branch passage 280. Further, the air-blowing system having discharge device is configured to blow off air containing charged fine water particles 40 into the inside of cabin 3 from air outlet 212.

To be more specific, in the same manner as the above-mentioned respective exemplary embodiments, electrostatic atomization device 30 is disposed outside air supply passage 260. With such a configuration, it is possible to suppress the exposure of electrostatic atomization device 30 to high temperature air or low humidity air which flows through air supply passage 260.

As shown in FIG. 11, in electrostatic atomization device 30 of the present exemplary embodiment, one end 51 of introducing pipe 50 is connected to electrostatic atomization device 30 which is disposed outside one branch pipe 250 which forms pipe portion 230, for example. On the other hand, other end 52 of introducing pipe 50 is disposed in branch passage 280 (air supply passage 260). With such a configuration, charged fine water particles 40 generated by electrostatic atomization device 30 are introduced into branch passage 280.

Also in introducing pipe 50 of the present exemplary embodiment, in a state where an other end 52 side of introducing pipe 50 is disposed in branch passage 280, introducing pipe 50 is disposed such that opening face 52*a* and a main stream direction (arrow direction) of air flow R1 which flows through branch passage 280 at center point C2 (predetermined point) of opening face 52*a* become substantially parallel (including parallel) to each other.

Further, as shown in FIG. 11, in the same manner as the sixth exemplary embodiment, branch pipe 250 of the seventh exemplary embodiment includes narrow portion 253 on straight line portion 251 of branch pipe 250 extending linearly. Narrow portion 253 is formed such that a flow passage cross-sectional area taken along a plane orthogonal to the main stream direction of air flow R1 is gradually decreased. To be more specific, protruding portion 254 which protrudes toward a branch passage 280 side is formed on a wall portion of straight line portion 251 on one side (on a side opposite to a side where introducing pipe 50 is inserted). With such a configuration, narrow portion 253 is formed in straight line portion 251 of branch pipe 250.

In this case, narrow portion 253 is formed such that a flow passage cross-sectional area of branch passage 280 is gradually decreased in a curved shape as narrow portion 253 extends toward top portion 254*a* of protruding portion 254 from an upstream side. Further, a flow passage cross-sectional area of branch passage 280 at narrow portion 253 becomes the minimum at top portion 254*a* of protruding portion 254. Thereafter, narrow portion 253 is formed such that flow passage cross-sectional area of narrow portion 253 is gradually increased in a curved shape as narrow portion 253 extends toward a downstream side from top portion 254*a* of protruding portion 254. Further, finally, a flow passage cross-sectional area of narrow portion 253 becomes equal to a flow passage cross-sectional area of usual straight line portion 251.

That is, branch pipe 250 of the present exemplary embodiment has narrow portion 253 having minimum portion 253*a* at which a flow passage cross-sectional area becomes the minimum.

Further, in a state where the other end 52 side of introducing pipe 50 is disposed in branch passage 280, opening face 52*a* of introducing pipe 50 is disposed in minimum portion 253*a* of narrow portion 253.

Further, introducing pipe 50 of the present exemplary embodiment has inclined portion 532 having an outer diameter thereof increased toward a one end 51 side from an opening face 52a side. Inclined portion 532 is formed at least at a portion of introducing pipe 50 which is disposed in the inside of air supply passage 260. To be more specific, inclined portion 532 having an outer diameter thereof increased toward the one end 51 side from an opening face 52a side is formed over the whole nozzle portion 530 of introducing pipe 50.

With such a configuration, also in the arrangement configuration of the present exemplary embodiment, it is possible to acquire substantially the same manner of operation and advantageous effects as the above-mentioned respective exemplary embodiments.

That is, introducing pipe 50 of the present exemplary embodiment has inclined portion 532 having an outer diameter thereof gradually increased from opening face 52a side toward the one end 51 side at least at a portion disposed in the inside of air supply passage 260 (corresponding to the nozzle portion in the first to sixth exemplary embodiments). Inclined portion 532 suppress a rapid change in a flowing direction of air flowing through air supply passage 260. That is, due to the flow of air along inclined portion 532, it is possible to prevent the flow of air from impinging on introducing pipe 50 from a front side (in a vertical direction) thus suppressing a rapid change in flowing direction of air. With such a configuration, a pressure loss of air flowing through air supply passage 260 can be reduced. As a result, a load applied to the air-blowing system, particularly, to blower 21 which generates a main stream of air flow R1 can be made small.

Further, due to the reduction of a load on blower 21, an output which blower 21 is required to possess can be reduced. With such a configuration, small sizing and reduction of cost of blower 21 can be realized.

Further, due to the formation of inclined portion 532, introducing pipe 50 is easily inserted into the inside of air supply passage 260. Accordingly, operability at the time of mounting introducing pipe 50 or the like is enhanced.

It is needless to say that a configuration may be adopted where introducing pipe 50 is inserted into the inside of air supply passage 260 by applying the configuration of inclined portion 532 of introducing pipe 50 of the present exemplary embodiment to the above-mentioned respective exemplary embodiments.

The preferred exemplary embodiments of the present invention have been described above. However, the present invention is not limited to the above-mentioned exemplary embodiments and various modifications are possible.

For example, in the above-mentioned respective exemplary embodiments, description is made by taking the device where the electrostatic atomization device is mounted on the vehicle-use air conditioner as the air-blowing system having discharge device as an example. However, the present invention is not limited to such an example. For example, a configuration may be adopted where an electrostatic atomization device is mounted on an air-blowing system other than a vehicle-use air conditioner. Further, a configuration may be adopted where an electrostatic atomization device is mounted on an air-blowing system in a civil-use field, a residential-use field and the like. Further, it is possible to adopt a configuration where a discharge device other than the electrostatic atomization device is mounted on an air-blowing system in a civil-use field, a vehicle-mounted field, a residential-use field and the like. As the air-blowing system and the discharge device, a conventionally-known device can be used.

In the above-mentioned exemplary embodiments, it has been not particularly referred to specifications (shapes, sizes, layout and the like) of the introducing pipe, the air supply passage, and other minute parts. However, it is needless to say that the specifications can be suitably changed.

As has been described heretofore, the air-blowing system having discharge device according to the present invention includes: an air supply passage having an air outlet from which air is blown off, and a discharge device provided for generating active ingredients and disposed outside the air supply passage. Further, the air-blowing system having discharge device includes an introducing pipe where one end of the introducing pipe is connected to the discharge device, the other end of the introducing pipe is disposed in the air supply passage, and active ingredients are introduced into the air supply passage. The other end of the introducing pipe includes an opening face. The introducing pipe is arranged such that, in a state where the other end side of the introducing pipe is disposed in the air supply passage, the opening face and a main stream direction of an air flow which flows through the air supply passage at a predetermined point of the opening face are substantially parallel to each other.

With such a configuration, in the opening face of the introducing pipe, a frictional force generated when air flowing through the air supply passage and air flowing through the introducing pipe are brought into contact with each other can be increased. Due to such a frictional force, air in the introducing pipe which is brought into contact with the opening face of the introducing pipe is easily induced into the air supply passage. Accordingly, air in the introducing pipe which is brought into contact with the opening face of the introducing pipe is induced into the air supply passage sequentially. With such a configuration, the flow of air toward the air supply passage is easily generated also in the inside of the discharge device connected to the introducing pipe. As a result, active ingredients generated by the discharge device can be introduced into the air supply passage without disposing a fan in the discharge device. Further, by disposing the introducing pipe at an arbitrary position of the air supply passage, active ingredients can be introduced into the inside of the air supply passage.

Further, the air-blowing system having discharge device of the present invention may be configured to set a predetermined point at a center point of the opening face.

With such a configuration, even when an air flow flows in a bending manner along the inside of the air supply passage, the whole surface of the opening face of the introducing pipe can be made to extend substantially along the main stream direction of the air flow.

For example, in a case where a predetermined point is set to an upstream end side of the opening face, when an air flow flows in a bending manner along the air supply passage, the extending direction of the opening face is separated from the main stream direction of an actual air flow at a downstream end of the opening face. Accordingly, the whole surface of the opening face of the introducing pipe cannot be made to extend along the main stream direction of an air flow. The same also goes for a case where a predetermined point is disposed at a downstream end of the opening face. With such a configuration, a frictional force for inducing air in the inside of the introducing pipe becomes small.

Accordingly, as described above, the predetermined point is set at the center point of the opening face. With such a configuration, a separation amount between the extending direction of the opening face of the introducing pipe and the main stream direction of an actual air flow on an upstream end and a downstream end of the opening face can be made relatively small. With such a configuration, the whole surface of the opening face of the introducing pipe can be made to extend substantially along the main stream direction of an air flow. Accordingly, a frictional force between both airs at respective points on the opening face is further increased. As a result, active ingredients generated by the discharge device can be made to flow into the air supply passage more efficiently.

Further, the air-blowing system having discharge device of the present invention is configured such that the introducing pipe has the protruding portion on the other end, the protruding portion linearly protruding toward the inside of the air supply passage from the wall portion which defines the air supply passage. Further, the protruding portion may be disposed in a state where the protruding portion orthogonally intersects with the tangential plane of the inner surface at an intersection between the center axis of the protruding portion and the inner surface of the wall portion.

Further, in the air-blowing system having discharge device of the present invention, the protruding portion may be disposed in an inclined manner with respect to the tangential plane of the inner surface at an intersection between the center axis of the protruding portion and the inner surface of the wall portion such that the other end of the protruding portion is disposed on a downstream side of the air supply passage.

With such a configuration, when the introducing pipe is disposed in the inside of the air supply passage, it is possible to suppress the displacement of a predetermined point of the opening face in the extending direction of the opening face from the main stream direction of an air flow. That is, the extending direction of the opening face can be disposed substantially parallel (including parallel) to the main stream direction of an air flow at a predetermined point of the opening face more easily.

Further, the air-blowing system having discharge device of the present invention may be configured such that the air supply passage has the narrow portion having a small flow passage cross-sectional area taken along a plane orthogonal to the main stream direction of the an air flow, and the opening face is disposed in the inside of the narrow portion.

With such a configuration, the opening face of the introducing pipe is disposed in a region where a flow speed of air becomes relatively fast in the air supply passage. Accordingly, in the opening face of the introducing pipe, a frictional force generated by contact between air flowing through the air supply passage and air in the introducing pipe can be further increased. With such a configuration, active ingredients generated by the discharge device can be made to flow into the air supply passage more efficiently.

Further, the air-blowing system having discharge device of the present invention may be configured such that the narrow portion has the minimum portion at which the small flow passage cross-sectional area becomes the minimum, and the opening face is disposed in the inside of the minimum portion.

With such a configuration, the opening face of the introducing pipe is disposed in a region where a flow speed of air becomes the fastest in the air supply passage. Accordingly, in the opening face of the introducing pipe, a frictional force generated by contact between air flowing through the air supply passage and air in the introducing pipe can be further increased. As a result, active ingredients generated by the discharge device can be made to flow into the air supply passage more efficiently.

Further, the air-blowing system having discharge device of the present invention may be configured such that at least a portion of the introducing pipe disposed in the inside of the air supply passage has the inclined portion at which an outer diameter is gradually increased from an opening face side toward one end side.

With such a configuration, it is possible to suppress a rapid change in flowing direction of air which flows through the air supply passage. With such a configuration, a pressure loss of air flowing through the air supply passage can be reduced. As a result, a load applied to the air-blowing system can be made small.

INDUSTRIAL APPLICABILITY

The present invention is useful in a field of an air-blowing system having discharge device which is required to satisfy the simplification of the configuration.

REFERENCE MARKS IN THE DRAWINGS

1: vehicle
2: instrument panel
3: cabin
10: air conditioner having discharge device (air-blowing system having discharge device)
20: vehicle-use air conditioner (air-blowing system)
21: blower
22: filter
23: evaporator
24: finisher
25: partition wall
25*a*: air direction adjusting plate
25*b*: horizontal partition wall
26: tab portion
27: link
30: electrostatic atomization device (discharge device)
40: charged fine water particle (active ingredient)
50: introducing pipe
51: one end
52: other end
52*a*: opening face
532: inclined portion
210: housing
211: suction port
212: air outlet
212*a*: opening portion
220: air conditioning portion
230: pipe portion
240: pipe body
250: branch pipe (wall portion)
250*a*: inner surface
251: straight line portion
252: bent portion
253: narrow portion
253*a*: minimum portion
254: protruding portion
254*a*: top portion
260: air supply passage
270: air supply passage body
280: branch passage
310: discharge portion
311: discharge electrode
311*a*: main body portion
311*b*: discharge electrode end portion
311*c*: sandwiched portion
312: counter electrode

312*a*: mist ejecting port
320: Peltier unit
330: cooling portion
331, 341: insulating plate
331*a*, 341*a*: circuit
332: cooling insulating plate
340: heat radiation portion
342: heat radiation plate
342*a*: heat radiation fin
350: support frame
351: partition wall
351*a*: communication hole
352: flange portion
352*a*: screw hole
353: screw
360: thermoelectric element
370: Peltier input lead line
380: high voltage applying portion
381: high voltage lead line
390: sealing resin
510: body portion
520: connecting portion
530: nozzle portion
531: protruding portion
C1: center axis
C2: center point
C3: center
C4: straight line
M1, M2: tangential plane
P1: intersection
R1: air flow
S1: discharge space
S2: sealing space

The invention claimed is:

1. An air-blowing system comprising:

an air supply passage having an air outlet from which air is blown off and an air inlet;

a discharge device provided for generating active ingredients and disposed outside the air supply passage; and an introducing pipe having a first end connected to the discharge device and disposed outside the air supply passage, and a second end disposed in the air supply passage, the introducing pipe being provided for introducing the active ingredients into the air supply passage, wherein the second end of the introducing pipe includes an opening face, and the introducing pipe is arranged such that, in a state where the second end of the introducing pipe is disposed in the air supply passage between the air inlet and the air outlet, the opening face and a main stream direction of an air flow which flows through the air supply passage at a predetermined point of the opening face are substantially parallel to each other.

2. The air-blowing system according to claim 1, wherein the predetermined point is set at a center point of the opening face.

3. The air-blowing system according to claim 1, wherein:

the introducing pipe has a protruding portion on the second end, the protruding portion linearly protruding toward an inside of the air supply passage from a wall portion which defines the air supply passage, and the protruding portion is disposed to orthogonally intersect with a tangential plane of an inner surface of the wall portion at an intersection between a center axis of the protruding portion and the inner surface of the wall portion.

4. The air-blowing system according to claim 1, wherein:

the introducing pipe has a protruding portion on the second end, the protruding portion linearly protruding toward an inside of the air supply passage from a wall portion which defines the air supply passage, and the protruding portion is disposed to be inclined with respect to a tangential plane of an inner surface of the wall portion at an intersection between a center axis of the protruding portion and the inner surface of the wall portion such that the second end is disposed on a downstream side of the air supply passage.

5. The air-blowing system according to claim 1, wherein:

the air supply passage has a narrow portion having a small flow passage cross-sectional area taken along a plane orthogonal to the main stream direction of the air flow, and the opening face is disposed in the narrow portion.

6. The air-blowing system according to claim 5, wherein:

the narrow portion has a minimum portion at which the small flow passage cross-sectional area is minimum, and the opening face is disposed in the minimum portion.

7. The air-blowing system according to claim 1, wherein at least a portion of the introducing pipe disposed in the air supply passage has an inclined portion at which an outer diameter is gradually increased from the opening face toward the one end.

8. The air-blowing system according to claim 1, wherein a disposition of the opening face in the air supply passage is where a flow speed of the air becomes fastest.

9. The air-blowing system according to claim 1, wherein:

the air supply passage is provided with a bent portion, the bent portion has inner and outer wall portions formed concentrically with a center, the introducing pipe is inserted orthogonally through the inner surface into the bent portion, and the opening face is disposed substantially parallel to a tangential plane of the inner surface where the introducing pipe is inserted.

10. The air-blowing system according to claim 1, wherein the discharge device is configured to generate ions.

11. The air-blowing system according to claim 1, wherein the discharge device is an electric atomizer.

12. The air-blowing system having discharge device according to claim 4, wherein the opening face of the second end of the introducing pipe is substantially parallel to the tangential plane of the inner surface of the wall portion.

* * * * *